United States Patent [19]
DeVore et al.

[11] Patent Number: 6,161,544
[45] Date of Patent: Dec. 19, 2000

[54] METHODS FOR ACCELERATED ORTHOKERATOLOGY

[75] Inventors: Dale DeVore, Chelmsford, Mass.; Rory H. Oefinger, Westerly, R.I.

[73] Assignee: Keratoform, Inc., Westerly, R.I.

[21] Appl. No.: 09/014,955

[22] Filed: Jan. 28, 1998

[51] Int. Cl.$^7$ ............................................. A61B 19/00
[52] U.S. Cl. ............................................. 128/898
[58] Field of Search ................ 128/898; 351/160 H, 351/160 R, 161, 162, 177; 424/94.62, 427

[56] References Cited

U.S. PATENT DOCUMENTS

| | | |
|---|---|---|
| 1,929,228 | 10/1933 | Wilhelm . |
| 3,302,646 | 2/1967 | Behney . |
| 3,416,530 | 12/1968 | Ness . |
| 3,485,244 | 12/1969 | Rosen . |
| 3,760,807 | 9/1973 | Neefe . |
| 3,776,230 | 12/1973 | Neefe . |
| 3,786,812 | 1/1974 | Neefe . |
| 3,831,604 | 8/1974 | Neefe . |
| 3,957,049 | 5/1976 | Neefe . |
| 4,484,922 | 11/1984 | Rosenwald . |
| 4,540,417 | 9/1985 | Poler . |
| 4,571,039 | 2/1986 | Poler . |
| 4,592,752 | 6/1986 | Neefe . |
| 4,713,446 | 12/1987 | DeVore et al. . |
| 4,851,513 | 7/1989 | DeVore et al. . |
| 4,969,912 | 11/1990 | Kelman et al. . |
| 5,163,956 | 11/1992 | Liu et al. . |
| 5,196,027 | 3/1993 | Thompson et al. . |
| 5,201,764 | 4/1993 | Kelman et al. . |
| 5,270,051 | 12/1993 | Harris . |
| 5,492,135 | 2/1996 | DeVore et al. . |
| 5,626,865 | 5/1997 | Harris et al. . |

FOREIGN PATENT DOCUMENTS

| | | |
|---|---|---|
| 861 753 | 1/1953 | Germany . |
| 2 308 144 | 1/1973 | Germany . |
| 24 26 757 | 12/1975 | Germany . |
| 1015284 | 12/1965 | United Kingdom . |

OTHER PUBLICATIONS

Kame, "Flattening the Cornea the Nonsurgical Way", Review of Optometry, Apr. 15, 1995.

Leslie Sabbagh, "FDA Trials to Begin for New, Nonsurgical Method of Correcting Refractive Error", Primary Care Optometry News, Jun., 1996, pp. 1, 21–23.

Primary Examiner—V. Millin
Assistant Examiner—Kelley O'Hara
Attorney, Agent, or Firm—Barlow, Josephs & Holmes, Ltd.

[57] ABSTRACT

An accelerated method of orthokeratology includes the steps of softening of the cornea with a softening agent, applying a mold to reshape the cornea to a desired anterior curvature, and rapidly restabilizing or "fixing" the corneal tissues so that the cornea retains its new configuration. A chemical softening agent, such as glutaric anhydride is applied to the cornea to soften the cornea, after which a specially designed mold of predetermined curvature and configuration is applied to the cornea. Slight downward pressure is applied to the mold for a predetermined period of time to re-shape the cornea. The mold is maintained in position while a stabilizing agent, such as a UV light source, is positioned above the mold. The stabilizing agent, i.e. UV light, is applied to the cornea for a predetermined time, wherein the stabilizing agent immediately restabilizes the corneal tissue so that the cornea immediately retains its shape upon removal of the mold. The stabilization process can also be used for patients having already undergone traditional orthokeratology to eliminate the need to continue wearing a retainer to maintain the shape of the cornea.

13 Claims, 11 Drawing Sheets

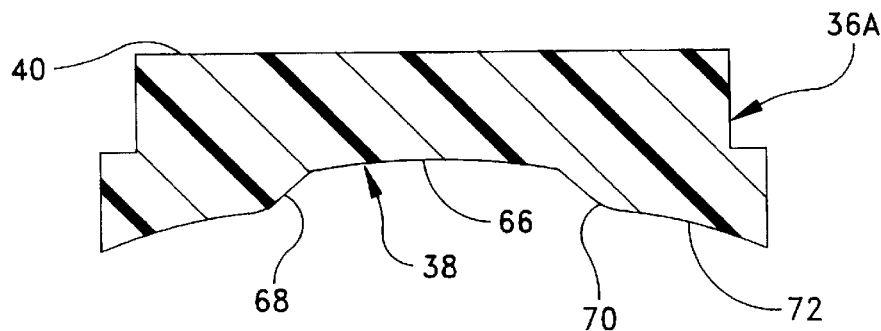
FIG. 8A
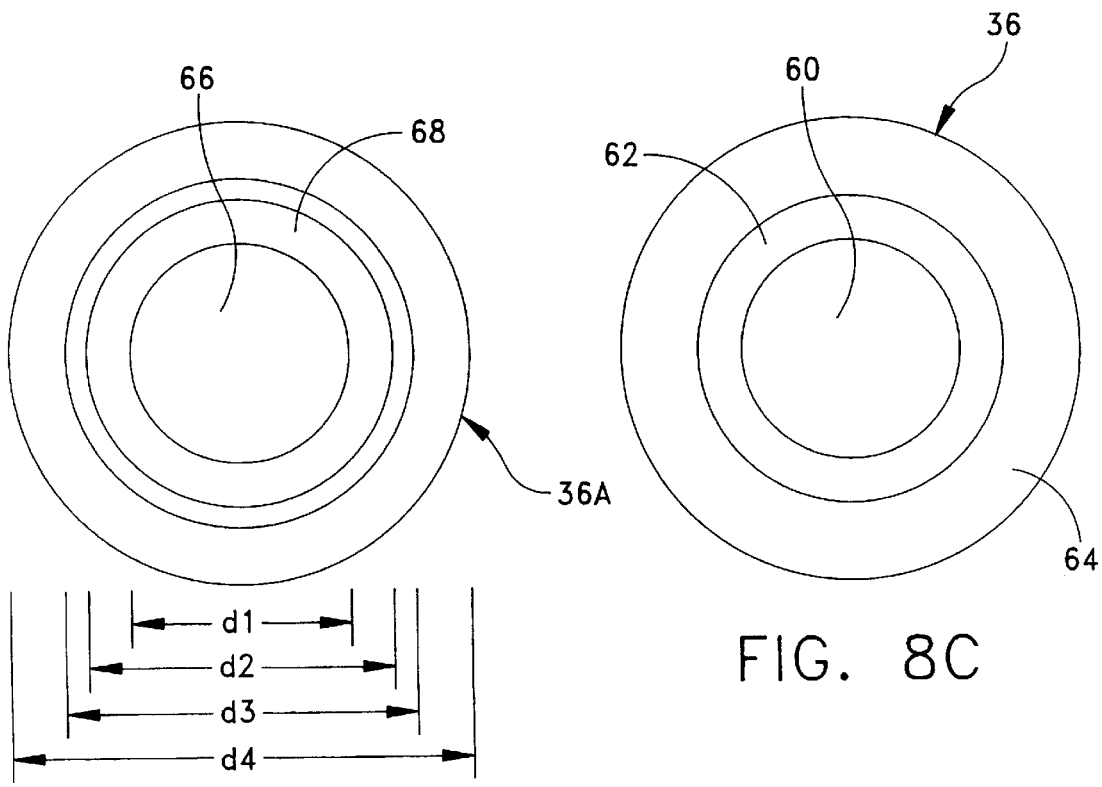
FIG. 8B
FIG. 8C

METHODS FOR ACCELERATED ORTHOKERATOLOGY

BACKGROUND AND SUMMARY OF THE INVENTION

The present invention relates to orthokeratology, i.e. shaping of the cornea to correct for refractive errors, and more particularly to an accelerated method of reshaping the corneal tissues wherein the cornea is softened, shaped with a mold, and thereafter rapidly stabilized so that the cornea immediately retains the new shape.

Millions of people worldwide have refractive errors of the eye which cause them to seek out corrective eyeglasses and/or contact lenses. Among the most common refractive errors are myopia (inability to see distant objects), hyperopia (inability to see near objects), and astigmatism (asymmetric sloping of the cornea whereby the curvature is different in different planes). Each of the above-noted defects is usually corrected by means of corrective eyeglasses or contact lenses. Corrective eyeglasses correct refractive errors by changing the angle of light with a lens before it reaches the cornea. Contact lenses correct refractive errors by replacing the misshapen anterior curvature of the cornea with a curvature which is calculated to render the eye emmetropic. While corrective eyeglasses and contact lenses are highly effective for temporarily correcting these problems, i.e. while the glasses or contacts are in place, the physical defects of the cornea are never corrected and thus require lifetime wear of the glasses or contacts. Accordingly, there has been an ongoing search for effective methods of correcting refractive errors of the eye by physically altering the anterior curvature of the cornea so that corrective lenses are no longer required.

Among the many solutions to refractive eye problems are surgical procedures in which the cornea is surgically altered. While effective, the existing surgical modification techniques have significant risk factors and drawbacks, including human error, infection, long healing time, and temporary loss of sight during recovery. Furthermore, there are significant psychological fears associated with voluntary eye surgery. The chances of permanently damaging the eye do not usually outweigh the discomfort of wearing glasses or contacts in most cases. For obvious reasons, invasive surgical modification of the cornea has not been well received as a purely voluntary procedure.

A non-invasive technique for physically altering the anterior curvature of the cornea which has received acceptance is Laser Photorefractive Keratectomy wherein an excimer laser is used to selectively strip away (ablate) outer layers of the cornea to produce a more spherical curvature. The laser method has achieved a high degree of success. However, there are certain drawbacks to this procedure, including temporary reductions of visual acuity during healing, delayed visual recovery, pain, stromal haze, temporary hyperopia, night glare, halos, and infectious keratitis.

A lesser known non-surgical technique, orthokeratology, which forms the general basis for the present invention, involves the use of a series of progressive contact lenses that are intended to gradually reshape the cornea and produce a more spherical anterior curvature. The process usually involves the fitting of 3 to 6 pairs of contact lenses, and usually takes approximately 3–6 months to achieve optimal reshaping. The theory behind Orthokeratology is that the cornea is very pliable and can be physically reshaped over time. The thickest layer of the cornea, known as the stroma, is formed from alternating lamella of fine collagen fibrils which form a pliable matrix of tissue. While the collagen tissues are pliable, they unfortunately also exhibit shape memory, and unless retainer lenses are worn daily to maintain the desired shape, the cornea will rapidly regress to the original shape.

Additional development work in the field of orthokeratology has yielded accelerated methods of orthokeratology wherein chemical, enzymatic and/or other agents are used to soften the cornea. For example, the Neefe U.S. Pat. Nos. 3,760,807, 3,776,230 and 3,831,604 collectively describe the use of chemicals such as proparacaine hydrochloride, dyclonine hydrochloride, chlorine in solution, the application of heat to the cornea through heated molds, the application of heat in the form of ultrasonic energy, and the use of proteolytic enzymes to soften the cornea for reshaping. Furthermore, the Kelman and DeVore U.S. Pat. Nos. 4,713,446, 4,851,513, 4,969,912, 5,201,764 and 5,492,135 each describe various chemical agents for treating and/or softening both natural and artificial collagen materials for ophthalmic uses.

Of the various prior art available in this subject area, the Harris U.S. Pat. Nos. 5,270,051 and 5,626,865 are believed to be the closest prior art to the subject matter of the invention of which the applicant is aware. The Harris patents describe a method of accelerated shaping of the cornea by releasing enzymes, such as hyalurodinase, into the cornea to temporarily soften the cornea, and thereafter fitting the cornea with a rigid contact lens which has a curvature that will correct the refractive error. The softened cornea then reshapes its curvature to the curvature of the contact lens rendering the eye emmetropic. The speed of the shaping process is significantly increased by the use of the softening agent, and reduces the treatment period from months to days. After shaping, a retainer lens is worn for a period of several days while the enzyme is allowed to dissipate from the cornea, and the cornea "hardens" to retain the new emmetropic configuration.

While softening of the corneal tissues does speed in reshaping of the cornea, there has been very little success in developing a successful method of rapidly restabilizing the corneal tissues in their new configuration after reshaping. The methods as described in the Harris U.S. Pat. Nos. 5,270,051 and 5,626,865 simply allow the softening agent to dissipate over time, after which time the lens can be removed. The only prior art known to the Applicant in the context of "active" corneal restabilization, is the Neefe U.S. Pat. No. 3,760,807 which describes a method of administering oral Vitamin C as a means for speeding the hardening of the cornea after use of the corneal softening agent has been discontinued. However, speeding up the hardening of the cornea in this context means to possibly reduce the hardening time from weeks to days.

The instant invention provides improved methods of accelerated orthokeratology which focus on rapidly restabilizing the corneal tissues in their new configuration after reshaping. The successful development of a rapid method of restabilizing the corneal tissues provides the final key step in a rapid non-surgical treatment alternative for physically reshaping of the cornea. In the context of the present invention, a patient could expect to enter the doctor's office on an outpatient basis, have the entire treatment completed within hours, and leave the office with a completely and reshaped cornea and no need for further use of contacts or glasses.

Generally speaking, the improved method as described herein comprise a three step process of: 1) softening or "destabilizing" the cornea with a chemical or enzymatic softening agent; 2) applying a mold to reshape the cornea to a desired anterior curvature; and 3) rapidly restabilizing the corneal tissues with a "stabilizing agent" which is effective for immediately initiating cross-linking of the collagen matrix. The term "stabilizing agent" as used herein is intended to include both chemical agents as well as external energy, such as light energy, applied to the cornea. More specifically, the contemplated agents for restabilizing the cornea include chemical cross linking agents, ultraviolet irradiation, thermal radiation, visible light irradiation, and microwave irradiation. The preferred method of restabilizing the cornea presently comprises exposure UV light energy, in conjunction with a photoactivator or initiator. The invention further provides novel apparatus for use in the described methods.

In the preferred method an annular staging device is aligned and secured with a biological glue over the cornea for guiding delivery of the softening agents, mold and UV light to the cornea. The staging device preferably includes an annular flexible gasket on the lower rim to prevent leakage of the chemicals introduced into the staging device. A chemical softening agent, such as glutaric anhydride is introduced into the staging device to soften the cornea. Glutaric anhydride is known to destabilize cross-links between the collagen fibrils, and acts to soften the corneal tissue enough to allow shaping with minimal external pressure. After treatment with the chemical softener, a specially designed mold of predetermined curvature and configuration is fitted into the staging device. Slight downward pressure is applied to the mold for a predetermined period of time (1–10 minutes) to re-shape the cornea. The mold is thereafter maintained in position while a UV light source is positioned above the mold within the staging device. The mold is preferably fashioned from a material which is transparent and non-UV absorbing, such as clear acrylic. UV light is applied to the cornea for a predetermined time wherein the UV light cross-links, the collagen fibrils and restabilizes the corneal tissue so that the cornea immediately and retains its new shape. The stabilization step can also be used for patients having already undergone long term orthokeratology to eliminate the need to continue wearing a retainer to maintain the shape of the cornea.

Accordingly, among the objects of the instant invention are: the provision of an accelerated method of orthokeratology including a means for rapidly restabilizing the cornea tissues after reshaping; the provision of such a method wherein the cornea is softened with a softening agent which destabilizes the collagen fibrils in the cornea; the provision of such a method wherein the softened cornea is thereafter molded with a mold having a predetermined curvature and configuration; the provision of such a method wherein the cornea is stabilized by applying UV light to cross-link the collagen fibril network; the provision of apparatus for performing the method including an staging device for limiting the treatment area of the cornea and preventing leakage of treatment chemicals outside of the designated area; and the provision of such a staging device wherein the staging device guides application of the mold and light energy to the cornea.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention:

FIG. 8A is a cross-sectional view of an alternative mold configuration;

FIG. 8B is a bottom view thereof showing the dimensions of the various peripheral curve zones;

FIG. 8C is a bottom view of a similar mold having only a single mid-peripheral curve;

DESCRIPTION OF THE PREFERRED EMBODIMENT

In accordance with the present invention, there is provided an improved method for accelerated orthokeratology. The improved method generally includes the three separate steps of: (1) softening the cornea so that the cornea can be shaped from a first configuration to a second emmetropic configuration; (2) reshaping the cornea by applying a mold to the cornea; and (3) restabilizing the corneal tissues so that they remain in their new configuration.

Figure 15:
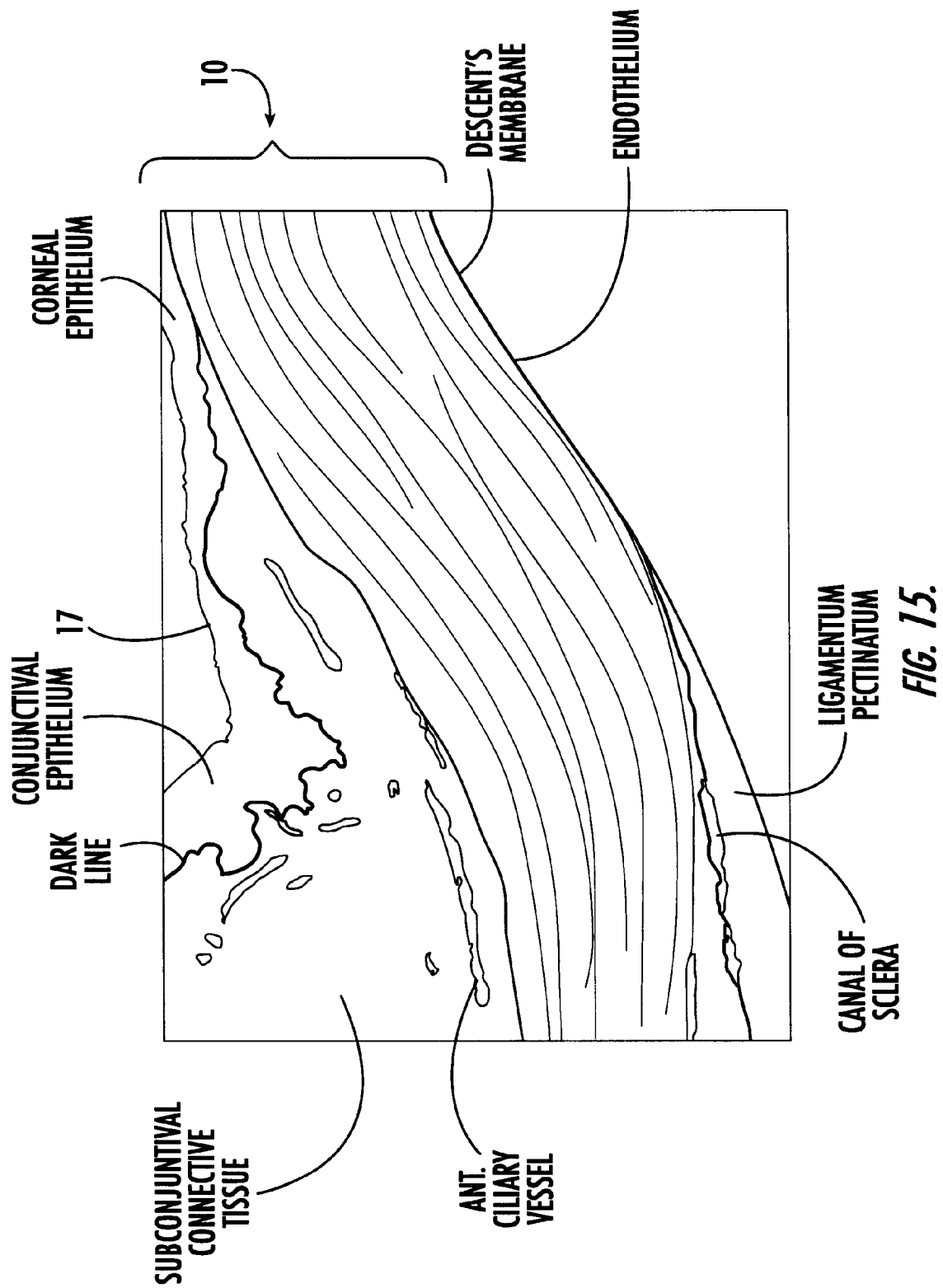
FIG. 15 is a microphotograph of a cross-section of the human cornea.
Figure 17:
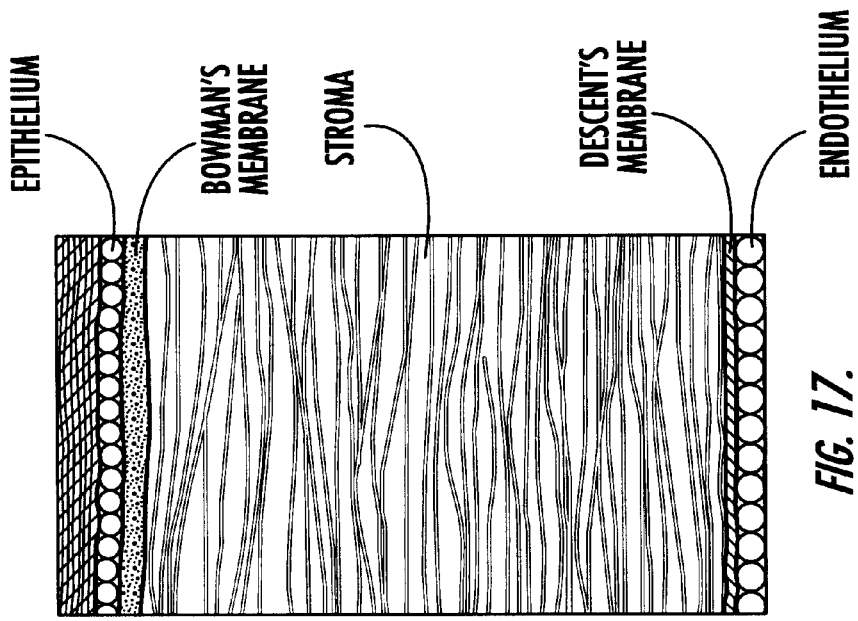
FIG. 17 is a schematic diagram showing a cross-section of the human cornea.
Figure 16:
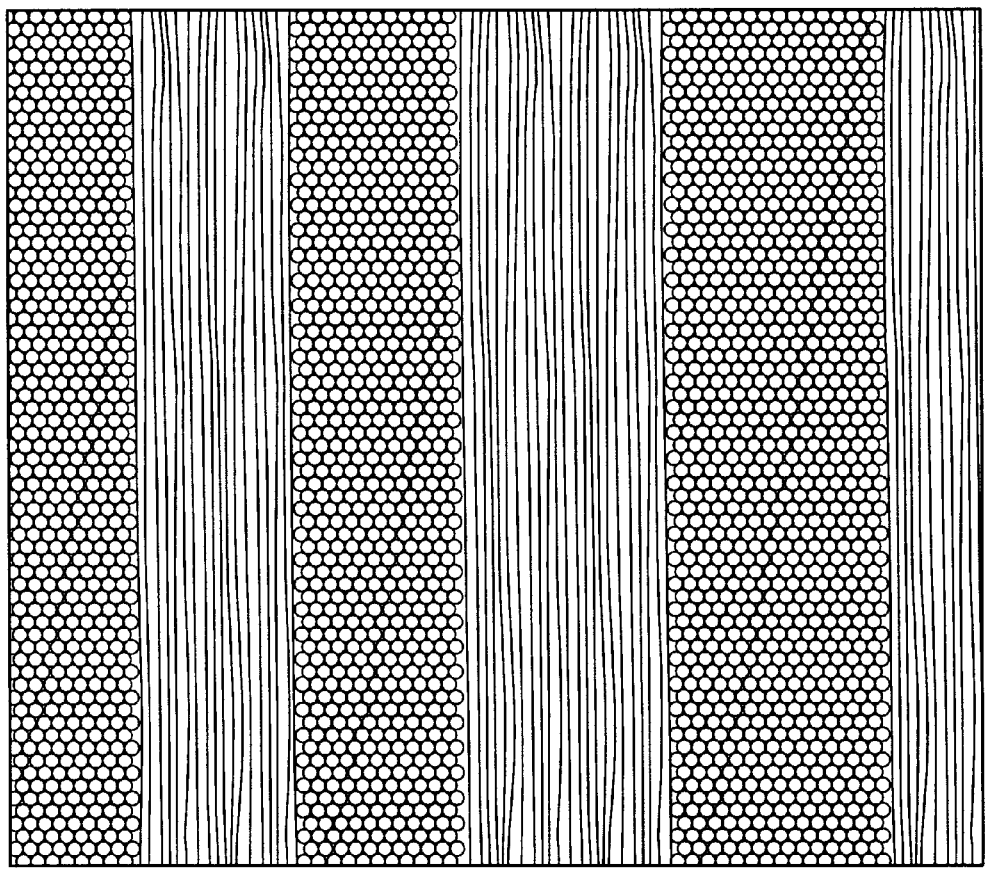
FIG. 16 is an enlargement of the microphotograph showing the collagen lamella of the stroma.

Referring to FIGS. 15–17, the cornea 10 is made up of 5 distinct layers of tissues, namely the epithelium, Bowman's Membrane, stroma, Descemet's Membrane, and the endothelium. In FIGS. 15 and 17, it is obvious that the thickest layer of the cornea 10 is the stroma 16. The stroma is comprised of alternating lamellae of collagenous tissue (about 200–250 in number), the planes of which are parallel to the surface of the cornea. Referring to FIG. 16, the lamellae are each composed of fine collagen fibrils and proteoglycans. The collagen fibrils of alternate lamellae make a right angle with each other. Each lamellae crosses the whole of the cornea, being about 2 $\mu$m thick. In the methods to be described herein, chemical agents which soften, degrade or "destabilize" the structural components of the stroma are topically administered to the cornea 10. The words soften, degrade, and destabilize are interchangeable for purposes of this specification, and they are all intended to denote a change in the corneal tissues which results in the cornea 10 becoming softer and more pliable so that the cornea can be reshaped from its' normal configuration to a second "emmetropic" configuration very quickly.

Chemical and/or Enzymatic Softening Agents

For purposes of the present invention, any one of a wide variety of chemical and/or enzymatic softening agents can be utilized to soften the corneal tissues. As previously described in the background, the Neefe U.S. Pat. Nos. 3,760,807, 3,776,230 and 3,831,604 collectively describe the use of chemicals such as proparacaine hydrochloride, dyclonine hydrochloride, chlorine in solution, and the use of proteolytic enzymes all to soften to cornea for reshaping. As also described previously herein, the U.S. patents to Harris describe the use of enzymes, such as hyalurodinase, for softening of the corneal tissues. Even further still, the Kelman and DeVore U.S. Pat. Nos. 4,713,446, 4,851,513, 4,969,912, 5,201,764, 5,354,336 and 5,492,135 each describe various chemical agents for treating and/or softening both natural and artificial collagen materials for ophthalmic uses. The teachings of all of these patents with respect to chemical destabilizing agents are incorporated herein by reference. While incorporated herein, the teachings of these patents are not intended to limit the scope of the term destabilizing agent, and the listings recited therein are not intended to be limiting.

Despite the multitude of different chemicals which could be utilized as destabilizing agents, the preferred families of destabilizing agents include anhydrides, acid chlorides, sulfonyl chlorides and sulfonic acids. The following lists of chemicals are intended to be representative of these types of chemicals, and are not intended to be limiting.

Suitable, but non-limiting examples of potential anhydrides include: Dichloroacetic Anhydride; Diglycolic Anhydride; Chlorodifluoroacetic Anhydride; Dichloroacetic Anhydride; Acetic Anhydride; Dichloromaleic Anhydride; Maleic Anhydride; Acetic Anhydride; Trichloroacetic Anhydride; Chloroacetic Anhydride; Acetic Anhydride; Succinic-D4 Anhydride; Chloroacetic Anhydride; Dimethyl Pyrocarbonate; (Acetic Anhydride)-D6; Iodoacetic Anhydride; Hexafluoroglutaric Anhydride; Trifluoroacetic Anhydride; Succinic Anhydride; 3-Chloro-Glutaric Anhydride; Bromomaleic Anhydride; Succinic Anhydride; Citraconic Anhydride; 2,3-Dimethylmaleic Anhydride; Diethyl Pyrocarbonate; Itaconic Anhydride; CIS-1,2-Cyclobutanedicarboxylic Anhydride; 3,4-Pyridinedicarboxylic Anhydride; Glutaric Anhydride; S-Acetylmercaptosuccinic Anhydride; 1-Cyclopentene-1,2-Dicarboxylic Anhydride; Methylsuccinic Anhydride; 2-(Acetylthio)succinic Anhydride; 1,3-Cyclopentanedicarboxylic Anhydride; 1,1-Bis-(2-Hydroxyethyl)-Urea; 2,2-Dimethylsuccinic Anhydride; 2,2-Dimethylglutaric Anhydride; Pentafluoropropionic Anhydride; 3-Methylglutaric Anhydride; 3,3-Dimethylglutaric Anhydride; (s)-(–)-2-(Trifluoroacetamido) succinic Anhydride; Propionic Anhydride; Tetrabromophthalic Anhydride; CIS-Aconitic Anhydride; Propionic Anhydride; Tetrachlorophthalic Anhydride; 6-Chloroisatoic Anhydride; Isatoic Anhydride; Heptafluorobutyric Anhydride; 5-Nitroisatoic Anhydride; EXO-3,6-Eposy, 1,2,3,6-Tetrahydrophthalic Anhydride; 4,5-Dichlorophthalic Anhydride; 6-Nitorisatoic Anhydride; CIS-1,2,3,6-Tetrahydrophthalic Anhydride; 3,6-Dichlorophthalic Anhydride; Phthalic Anhydride; 3-Cyclohexene-1,2-Dicarboxylic Anhydride; 3-Chlorophthalic Anhydride; Phthalic Anhydride; 3,4,5,6-Tetrahydrophthalic Anhydride; 3-Nitrophthalic Anhydride; 3-Hydroxyphthalic Anhydride; 3,6-Endoxohexahydrophthalic Anhydride; 4-Nitrophthalic Anhydride; 1,2,3,4-Cyclobutanetetracarboxylic Dianhydride; (+)-Diacetyl-L-Tartaric Anhydride; 5-Chloroisatoic Anhydride; Tetrahydrofuran-2,3,4,5-Tetracarboxylic Dianhydride; CIS-1,2-Cyclohexanedicarboxylic Anhydride; Isobutyric Anhydride; 3-Methoxyphthalic Anhydride; Crotonic Anhydride; Butyric Anhydride; 2-Bromo-5-Norbornene-2,3-Dicarboxylic Anhydride; (+/–)-Trans-1,2-Cyclohexanedicarboxylic Anhydride; 1,4,5,6,7,7-Hexachloro-5-Norbornene-2,3-Dicarboxylic Anhydride; 3-Amino-5-Chloro-N-Methylisatoic Anhydride; Methacrylic Anhydride; Trimellitic Anhydride Chloride; N-Methylisatoic Anhydride; (+/–)-Isobutenylsuccinic Anhydride; 1,2,4-Benzenetricarboxylic Anhydride; CIS-5-Norbornene-Endo-2,3-Dicarboxylic Anhydride; 1,2-Cyclohexanedicarboxylic Anhydride; 1-Methyl-6-Nitroisatoic Anhydride; 3,5-Diacetyltetrahydropyran-2,4,6-Trione; 3-Ethyl-3-Methylglutaric Anhydride; Homophthalic Anhydride; 4-Methyl-1,2,3,6-Tetrahydrophthalic Anhydride; Butyric Anhydride; 4-Methylphthalic Anhydride; 5-Methyl-3A,4,7,7A-Tetrahydrophthalic Anhydride; 2-Furoic Anhydride; 3,6-Dimethyl-4-Cyclohexene-1,2-Dicarboxylic Anhydride; Norbornance-2,3-Dicarboxylic Anhydride; 2-Cyonoacetyl N-(4-Fluorophenyl)Carbamate; Endo-3,6,Dimethyl-3,6-Endoxohexahydrophthalic Anhydride; 3,6-Encoso-3-Methylhexahydrophthalic Anhydride; 2-Cyanoacetyl N-Phenylcarbamate; 2-Methyl-8-Oxaspiro (4.5)Decane-7,9-Dione; (+/–)-Hexahydro-4-Methylphthalic Anhydride; 3,6-Dimethylphthalic Anhydride; 8-Methyl-2-Oxaspiro(4.5)Decane-1,3-Dione; 3,3-Tetramethyleneglutaric Anhydride; Bicyclo(2.2.2)Octa-2,5-Diene-2,3-Dicarboxylic Anhydride; 3-Methoxy-5-Methylhexahydrophthalic Anhydride; 1,2,4,5-Benzenetetracarboxylic Di-Anhydride; Endo-Bicyclo(2.2.2) Oct-5-Ene-2,3-Dicarboxylic Anhydride; Trimethylacetic Anhydride; 1,2,4,5-Benzenetetracarboxylic Dianhydride; methyl-5-Norbornene-2,3-Dicarboxylic Anhydride; Valeric Anhydride; 2-Cyanoacetyl N-(2,3-Dichlorophenyl) Carbamate; Ethylenediaminetetraacetic Dianhydride; (S)-(+)-2-Methylbutyric Anhydride; 2-Phenylglutaric Anhydride; 1,8-Naphthalic Anhydride; Isovaleric Anhydride; 2-Benzylsuccinic Anhydride; 2,3-Naphthalic Anhydride; Di-Tert-Butyl Dicarbonate; 4,7-Dihydro-4,7A,7B-Trimethyl-4,7-Epoxyisobenzofuran-1,3(7A,7B)-Dione; 4-Mercapto-1,8,Naphthalic Anhydride; Di-Tert-Butyl Dicarbonate; 3-(Tert-Butyldimethylsilyoxy)Glutaric; 4-Sulfo-1,8-Naphthalic Anhydride; Di-Tert-Butyl Dicarbonate; 4-Bromo-1,8-Naphthalic Anhydride; 4-Amino-1,8-Naphthalic Anhydride; 2-Cyanocetyl N-(P-Tolyl) Carbamate; 4-Chloro-1,8-Naphthalic Anhydride; 2-Phthalimidosuccinic Anhydride; 2-Cyanoacetyl N-(4-Methoxyphenyl)Carbamate; 4-Nitro-1,8-Naphthalic Anhydride; 4-Amino-3,6-Disulfo 1,8-Naphthalic Anhydride; 2-Cyanocetyl N-(3-Methoxyphenyl)Carbamamte; 3-Nitro-1,8-Naphthalic Anhydride; Bicyclo(2.2.2)Oct-7-Ene-2,3,5, 6-Tetracarboxylic Dianhydride; Hexachlorohexahydro-1,4-Methanonaphthalene-6,7-Dicarboxylic Anhydride; Diphenic Anhydride; 2-(4-Acetoxyphenyl)Succinic Anhydride; N-Phthaloyl-Dl-Glutamic Anhydride; 4-methylfuro (3',4':5,6)Naphtho(2,3-D)(1,3)Dioxole-1,3(1H,3H)-Dione; Carbobenzyloxy-L-Aspartic Anhydride; Carbobenzyloxy-L-Glutamic Anhydride; 5-Bromo-1,2,3,4-Tetrahydro-1,4-Ethenonaphthalene-2,3-Dicarboxylic Anhydride; Bicyclo (4.2.2)Dec-7-Ene-9,10-Dicarboxylic Anhydride; 9-Isopropyl-3-Oxaspiro(5.5)Undecane-2,4-Dione; 5-Nitro-1,2,3,4-Tetrahydro-1,4-Ethenonaphthalene-2,3-Dicarboxylic Anhydride; 3-((Ethoxycarbonyl) oxycarbonyl))-2,2,5,5-Tetramethyl-3-Pyrrolin-1-Yloxy, FR; 1,4,5,8-Naphthalenetetracarboxylic Dianhydride; 5-Nitro-10-Oxo-1,2,3,4-Tetrahydro-1,4-Ethanonaphthalene2, 3dicarboxylic Anhydride; 2-(1-Octenyl)Succinic Anhydride; BIS(2,6-Dichlorobenzoic Anhydride; Benzoic Anhydride; 3-Methoxy-1,2,3,6-Tetrahydro-5-(Trimethylsilyoxy)phthalic Anhydride; 4-Bromobenzoic Anhydride; 4-(2-Hydroxyethylthio)-1,8-Naphthalic Anhydride; Hexanoic Anhydride; 3,5-Dinitrobenzoyl N-(2-Chlorophenyl)Carbamate; and Diethylenetriaminepentaacetic Dianhydride Suitable, but non-limiting examples of potential acid chlorides include: Propionyl Chloride; Methacryloyl Chloride; Acryloyl Chloride; Methoxyacetyl Chloride; Methacryloyl Chloride; Methyloxalyl Chloride; Heptafluorobutyrl Chloride; Cyclopropanecarbonyl Chloride; 2,3 Dichloropropionyl Chloride; 4,4,4-Trifluorocrotonyl Chloride; 3-Bromopropionyl Chloride; Fumaryl Chloride; Acetoxyacetyl Chloride; (=/-)-2-Bromopropionyl Chloride; 4,4,4-Trifluorobutyrl Chloride; Ethyl Oxalyl Chloride; 2-Chloropropionyl Chloride; 4-Bromobutyrl Chloride; 3-Chloropropionyl Chloride; Crotonyl Chloride; 4-Chlorobutyrl Chloride; 5-(Chlorocarbonyl)Uracil; Ethyl Malonyl Chloride; 4-Chlorobutyrl Chloride; 2-Thiophenecarbonyl Chloride; 3-Carbomethoxypropionyl Chloride; Butyrl Chloride; 2-Furoyl Chloride; 3,3-Dichloropivaloyl Chloride; Isobutyrl Chloride; Itaconyl Chloride; 2,2-Bis(Chloromethyl)Propionyl Chloride; Butyryl Chloride; Blutaryl Dichloride; 5-Bromovaleryl Chloride; Butyryl Chloride; 3,3-Dimethylacryloyl Chloride; 4-Morpholinecarbonyl Chloride; Cyclobutanecarbonyl Chloride; 5-Chlorovaleryl Chloride; 5-Nitro-2-Furoyl Chloride; Ethyl Malonyl Chloride; 3-Chloropivaloyl Chloride; Trans-1,2-Cyclobutanedicarbonyl Dichloride; Hexanoyl Chloride; Valeryl Chloride; Adipoyl Chloride; Hexanoyl Chloride; Isovaleryl Chloride; Alpha,Alpha-Dimethylsuccinyl Chloride; Tert-Butylacetyl Chloride; Trimethylacetyl Chloride; Cyclopentanecarbonyl Chloride; 2-Ethylbutyrl Chloride; 3,4-Dichloro-2,5-Thiophenedicarbonyl Chloride; Ethylsuccinyl Chloride; Benzoyl-D5 Chloride; Nicontinoyl Chloride Hydrochloride; 1-Chlorocarbonyl-1-Methylethyl Acetate; Pentafluorobenzoyl Chloride; Isonicotinoyl Chloride Hydrochloride; Methyl 4-(Chloroformly)Butyrate; Pentachlorobenzoyl Chloride; 2-Thiopheneacetyl Chloride; 6-Bromohexanoyl Chloride; 2,3,4,5-Tetrafluorobenzoyl Chloride; 2,4-Difluorobenzoyl Chloride; 2,6-Dichlorobenzoyl Chloride; 2,3,6-Trifluorobenzoyl Chloride; 3,4-Difluorobenzoyl Chloride; 3,4-Dichlorobenzoyl Chloride; 2,3,4-Trifluorobenzoyl Chloride; 3,5-Difluorobenzoyl Chloride; 3-Bromobenzoyl Chloride; 3,4,5-Tridobenzoyl Chloride; 2,3-Difluorobenzoyl Chloride; 2-Bromobenzoyl Chloride; 2,4-Dichloro-5-Fluorobenzoyl Chloride; 3,5-Dinitorbenzoyl Chloride; 4-Bromobenzoyl Chloride; 2,4,6-Trichloribenzoyl Chloride; 2,6-Pyridnedicarbony Dichloride; 4-Fluorobenzoyl Chloride; 2,6-Difluorobenzoyl Chloride; 2,4-Dichlorobenzoyl Chloride; 2-Flurobenzyol Chloride; 2,5-Difluorobenzoyl Chloride; 3,4-Dichlorobenzoyl Chloride; 3-Fluorobenzoyl Chloride; 2-Nitrobenzoyl Chloride; Benzoyl Chloride; 4-Fluorobenzoyl-Carbonyl-13C Chloride; 2-Chlorobenzoyl Chloride; (s)-(-)-(Trifluoroacetyl)Prolyl Chlorde, 01.M Solution in Dichloromethane; 3-(Fluorosulfonyl)Benzoyl Chloride; 4-Chlorobenzoyl Chloride; 3-(2-Furyl)Alany Chloride Hydrochloride; 4-(Fluorosulfonyl)Benzoyl Chloride; 3-Chlorobenzoyl Chloride; Diethylmalonyl Dichloride; 2-lodobenzoyl Chloride; Benzoyl Chloride; 3-Methyladipoyl Chloride; 4-Iodobenzoyl Chloride; Benzoyl Chloride; Pimeloyl Chloride; 4-Nitrobenzoyl Chloride; Benzoyl-Carbonyl-13C Chloride; Cyclohexanecarbonyl Chloride; 3-Nitrobenzoyl Chloride; Benzoyl Chloride; 4-Methyl-4-Nitrohexanoyl Chloride; 4-Cyanobenzoyl Chloride; (+/-)-2-Chloro-2-Phenylacetyl Chloride; Heptanoyl Chloride; 3-Cyanobenzoyl Chloride; 4-Chlorophenoxyacetyl Chloride; Perfluorooctanoyl Chloride; Terephthaloyl Chloride; Para-Toluoyl Chloride; 2,3,5, 6-Tetrachloroterephthaloyl Chloride; Isophthaloyl Dichloride; Ortho-Toluoyl Chloride; Pentafluorophenylacetyl Chloride; Phthaloyl Dichloride; Meta-Toluoyl Chloride; 4-(Trifluoromethly)Benzoyl Chloride; 1,4-Phenylene BIS (Chloroformate); Pheylacetyl Chloride; 2-(Trifluoromethyl) Benzoyl Chloride; 4-(Trichloromethoxy)Benzoyl Chloride; Phenoxyacetyl Chloride; 3-(Trifluoromethyl)Benzoyl Chloride; 2-(2,4,5-Trichlorophenoxy)Acetyl Chloride; and M-Anisoyl Chloride.

Suitable, but non-limiting examples of potential sulfonyl chlorides include 4-Chlorobenzenesulfonyl Chloride; 4-Chloro-3-(Chlorosulfonyl)-5-Nitrobenzoic Acid; 3-Fluorosulfonylbenzenesulfonyl Chloride; 4-Chlorobenzenesulfonyl Chloride; 3-(Fluorosulfonyl) benzoyl Chloride; 4-Fluorosulfonylbenzenesuofonyl Chloride; 4-Amino-6-Chloro-1,3-Benzenedisulfonyl Chloride; 4-(Fluorosulfonyl)benzoyl Chloride; O-Fluorosulfonylbenzenesulfonyl Chloride; 3-Amino-4-Chlorobenzenesulfonyl; 2-Chloro-5-(Fluorosulfonyl)-Benzoic Acid; Pipsyl Chloride; Benzenesulfonyl Chloride; 4-(Chlorosulfonyl)phenyl Isocyanate; 4-Nitrobenzenesulfonyl Chloride; Benzenesulfonyl Chloride; 3,5-Dinitro-P-Toluenesulfonyl Chloride; 3-Nitrobenzenesulfonyl Chloride; 2-Acetamido-4-Methyl-5-Thiazolesulfonyl Chloride; 4-(Chlorosulfonyl)benzoic Acid; 2-Nitrobenzenesulfonyl Chloride; 2-Nitro-4-(Trifluoromethyl)Benzene-Sulfonyl Chloride; 3-(Chlorosulfonyl)-Benzoic Acid; Methyl 2-(Chlorosulfonyl)benzoate; 8-Quinolinesulfonyl Chloride; Alpha-Toluenesulfonyl Chloride; 3-(Chlorosulfonyl)-P-Anisic Acid; 4-(2,2-Dichlorocyclopropyl)-Benzenesulfonyl Chloride; P-Toluenesulfonyl Chloride; N-Acetylsulfanilyl Chloride; 2,4-Mesitylenedisulfonyl Chloride; O-Toluenesulfonyl Chloride; 2,5-Dimethoxy-4-Nitrobenzenesulfonyl Chloride; 2-Mesitylenesulfonyl Chloride; P-Toluenesulfonyl Chloride; 4-Dimethylamino-3-Nitrobenzenesulfonyl Chloride; 6-Diazo-5,6-Dihyrdo-5-Oxo-1-Naphthalenesulfonyl Chloride; 4-Methoxybenzenesulfonyl Chloride; 2,5-Dimethylbenzenesulfonyl Chloride; 2,6-Naphthalenedisulfonyl Chloride; 3,5-Dicarboxybenzenesulfonyl Chloride; 2,5-Dimethoxybenzenesulfonyl Chloride; 2-Naphthalenesulfonyl Chloride; Beta-Styrenesulfonyl Chloride; 5-Methylsulfonyl-Ortho-Toluenesulfonyl Chloride; 1-Naphthalenesulfonyl Chloride; 2,8,-Dibenzofurandisulfonyl Chloride; 4-(Dimethyllamino) azobenzene-4-Sulfonyl Chloride; 4-Tert-Butylbenzenesulfonyl Chloride; 4-(4-Chloro-5,7-Dibromo-2-Quinolyl)-Benzenesulfonyl Fluoride; 4-Sec-Butylbenzenesulfonyl Chloride; 4,4'-Biphenyldisulfonyl Chloride; 4-(4-Chloro-6-Nitro-2-Quinolyl)-Benzenesulfonyl Fluoride; (+)-10-Camphosulfonyl Chloride; 4,4'-Oxybis(Benzenesulfonyl Chloride); 4-Chloro-6-Fluorosulfonyl-2-(4-Nitrophenyl)quinoline; (-)-10-

Camphorsulfonyl Chloride; 4-(Phenylazo)Benzenesulfonyl Chloride; 4-Chloro-2-Phenylquinoline-4',6-Disulfonyl Fluoride; (+/−)-10-Camphorsulfonyl Chloride; Dansyl Chloride; 4-Chloro-2-Phenyl-6-Quinolinesulfonyl Fluoride; 1-Chloro-4-Fluorosulfonyl-2-Naphthoyl chloride; 4,4'-Methylenebis(Benzenesulfonyl Chloride); 2,4,6-Triisopropylbenzenesulfonyl Chloride; Pentamethylbenzenesulfonyl Chloride; 2-(Chlorosulfonyl)Anthraquinone; 4-Chloro-2-M-Tolyl)-6-Quinolinesolfonyl Fluoride; 4-Chloro-6-Fluorosulfonyl-2-(4-Ethoxy-3-Methoxyphenyl) Quinolin; 5-(Chlorosulfonyl)-2-(Hexadecycloxy)Benzoic Acid; 4-Chloro-2-({-Tolyl)-6-Quinolinesulfonyl Fluoride; 5,7,7-Trimethyl-2-(1,3,3-Trimethlbutyl)-1-Octancesulfonyl Chloride; 3-Chlorosulfonyl-4-Hexadecycloxybenzoic Acid; 5-Benzoyloxy-1-(3-Chlorosulfonylphenyl)-3-Methylpyrazole; 4-Chloro-2(4-(N,N-Diethylaminosulfonyl)-Phenyl)-6-Quinolinesulfonyl Fluoride; 5-(Chlorosulfonyl)-2-(Hexadecyclsulfonyl)Benzoic Acid; 1-Hexadecanesulfonyl Chloride; 2-(4-Benzyloxyphenyl)-4-Chloro-6-Quinolinesulfonyl Fluoride; Methyl 3-Chlorosulfonyl-4-(Hexadecyloxy)Benzoate; 3-(4-Chlorophenylcarbamoyl)-4-Hydroxy-1-Naphthalenesulfonyl Fluoride; 4-(Hexadecyloxy) Benzenesulfonyl Chloride; 3-Nitro-4-(Octadecylamino) Benzenesulfonyl Chloride; Methyl 4-(4-Chloro-6-Fluorosulfonyl-2-Quinolyl)Benzoate; 4-(2,5-Dichlorophenylazo)-4-Fluorosulfonyl-1-Hydroxy-2-Naphthanilide; 4-(4-Chloro-5,7-Dimethyl-2-Quinolyl)-Benzenesulfonyl Fluoride; 5-Fluorosulfonyl-2-(Hexadecyloxy)Benzoyl Chloride; Ethyl 4-Chloro-2-(4-Fluorosulfonylphenyl)-6-Quinolinecarboxylate; 5-Chlorosulfonyl-2-(Hexadecylsulfonyl)Benzoyl Chloride; Oxalyl Chloride; Acetly-2-13C Chloride; Chlorocarbonylsulfenyl Chloride; Trichloroacetyl Chloride; Acetyl-1-13C Chloride; Methanesulfonyl Chloride; Dichloroacetyl Chloride; Acetyl-13C2 Chloride; Acetyl-D3 Chloride; Bromoacetyl Chloride; Acetyl Chloride; Trifluoroacetyl Chloride; Chloroacetyl Chloride; Trichloroacryloyl Chloride; Oxalyl Chloride; Chlorosulfonylacetyl Chloride; Pentachloropropionyl Chloride; Oxalyl Chloride; Acetyl Chloride; Malonyl Cichloride; Oxalyl Chloride; Acetyl Chloride; and 2,3-Dibromopropionyl Chloride.

Suitable, but non-limiting examples of potential sulfonyl acids include 4,6-Diamino-2-Methylthiopyrimidine-5-Sulfonic Acid; 4-Pyridylhydroxymethanesulfonic Aceid; Sulfoacetic Acid, Pyridine Complex; 3,3-Oxetanebis (Methanesulfonic Acid)Disodium Salt; 2,5-Dimethyl-3-Thiophenesulfonic Acid Sodium Salt; 2-Pyrimidinesulfonic Acid, Sodium Sale; 1-Fluoropyridinium Triflate; Mes Monohydrate; 2-Thiophenesulfonic Acid, Sodium Salt; 3-Sulfoisonicotinic Acid, Barium Salt; 3-Sulfobenzoic Acid; (+/−)-1-Hyrdoxy-2,5-Dioxo-3-Pyrrolidine-Sulfonic Acid, Monosodium Salt; (1-Methylpyridinium 3-Sulfonate); 6-Acetamido-3-Pyridinesulfonic Acid; 5-Formyl-2-Furansulfonic Acid; 5-Methyl-3-Pyridinesulfonic Acid; 4-Pyridineethanesulfonic Acid; 3-Pyridinesulfonic Acid; 2-Pyridylhydorxymethanesulfonic Acid; 2-Pyridineethanesulfonic Acid; 3-Pyridinesulfonic Acid, Sodium Salt; 3-Pyridylhydroxymethanesulffonic Acid; Isonicotinic Acid 2-(Sulfomethyl)-Hydrazide, Calcium Salt Dihyrdate; Hepes; 1-(2,5-Dichloro-4-Sulfophenyl)-5-Pyrazolone-3-Carboxylic Acid; Mops (4-Morpholinepropanesulfonic Acid); Hepes, Sodium Salt; 5-Oxo-1-(4-Sulfophenyl)-2-Pyrazoline-3-Carboxylic Acid; Mops. Sodium Salt, Monohyrdate, (4-Morpholinepropanesulfonic Acid); Pipes (1,4-Piperazinebis-(Ethanesulfonic Acid)); 5-Oxo-1-(4-Sulfophenyl)-2-Pyrazoline-3-Carboxylic Acid, Lead Salt; Mopso, (Beta-Hyroxy-4-Morpholine-Propanesulfonic Acid); Pipes, Disodium Salt Monohyrdate; 4-Chloro-3-(3-Methly-5-Oxo-2-Pyrazolin-1-Yl)-Benzesulfonic Acid; 1-Allylpyridinium 3-Sulfonte; N(4-Amino-S-Triazin-2-Yl)-Sulfanilic Acid; 4-(3-Methyl-5-Oxo-2-Pyrazolin-1-Yl)-Benzenesulfonic Acid; 1-(3-Sulfopropyl)Pyridinium Hydroxide; Ethyl 2-Sulfobenzoate, Sodium Sale; 3-(5-Imino-3-Methyl-2-Pyrazolin-1-YL)Benzenesulfonic Acid; 2-Pyridinealdoxime Methyl Methanke-Sulfonate; 2-Methyl-1-(3-Sulfopropyl)Pyridinium Hydroxide, Inner Salt; Pyridinium 3-Nitrobenzenesulfonate; 1-Piperidinepropanesulfonic Acid; Epps (4-(2-Hyrdoxyethyl)-1-Piperazine-Propanesulfonic Acid); 2-Ethyl-5-Phenylisoxazolium 3'-Sulfonate; 1-Ethyl-2-Methly-3-(3-Sulfopropyl)Benzimidazole; Acid Orange 74; 2-Ethyl-5-Phenylisoxazolium 4'-Sulfonate Monohydrate; 4-(5-Hyroxy-1-Phenyl-1,2,3-Trizol-4-Ylozo) Benzenesulfonic Acid, Sodium Salt; Tartrazine; Pyridinium P-Toluenesulfonate; 1,4-Dimethylpyridinium P-Toluenesulfonate; Acid Yellow 34; Methanesulfonic (4-Aminophenyl-SulfopropylThizdiasol-2-In-5-Ylidene) Hydrazide; 4-Hyroxy-2-Phenyl-6-Quinolinesulfonic Acid; Mordant Red 19; 4,5-Dihyrdoxy-3-(2-Thiazolylazo)-2,7-Naphthalenedisulfonic Acid, Sodium Salt; 3-Methoxycarbonyl-1-Methylpyridinium Para-Toluenesulfonate; 1-Phenyl-3-(3-Sulfobenzamido)-2-Pyrazolin-5-One, Barium Salt; N-(4-Chlorobenzylideneamino)-Sulfanilic Acid, Pyridinium Salt; 3-(2-Pyridyl)-5,6-Bis(5-Sulfo-2-Furyl)-1,2,4-Triazine Dina Salt/3H20; Flavazin L; 2-Fluoro-1-Methylpyridinium P-Toluene-Sulfonate; Acid Red 183; 5-Tridecyl-1,2-Oxathiolane-2,2-Dioxide; N-Antipyrinyl-N-Methylaminomethanesulfonic Acid, Sodium Salt Monohydrate; Acid Yellow 17; 4-((4-Chlorobenzylidene)-3-Methly-1-(4-Sulfophenyl)-2-Pyrazolin-5-One; Reatcie Blue 4; Cibacron Brilliant Yellos 3GP; 2-(3-Sulfobenzoyl)Pyridine 2-Pyridyl-Hydrazone Dihyrdate; Acid Yellow 40; 2-5,6-Bix-4-Sulfophenyl-1,2,4-Triazin-3-YL-4-Sulfophenyl Pyridine/3NA/Ind.Grad.; 4-(1-Benzyl-5-Oxo-2-Pyrazolin-3-Ylcarbamoyl)Benzenesulfonic Acid, Barium Salt; (Bis) (Cyanoethyl)AminoBenzylidne)-Oxo-Sulfophenyl-Pyrazoline-Carboxylic Acid, NA; 1,1'Ethylenedipyridinium Di-P-Toluenesulfonate; 2,6-Diamino-3-(4-(2-Diethylaminoethoxy)-Phenylazo)Pyridine Methanesulfonate; Acid Yellow 76; Merocyanine 540; Palatine Fast Yellow Bln; Acid Yellow 25; 1-Hexadecanesulfonic (Fluorophenyl) (Sulfopropyl)Thiadiazol-2-Ylidene) Hydrazide; 3-(2-Pyridyl)-5,6-Diphenyl-1,2,4-Triazine-P,P'-Disulfonic Acid, 1-NA XH20; 2-Hexadecylthio-5-Sulfobenzoic Acid, Pyridine Salt; Reative Blue 2; 5-Phenyl-3-(4-Phenyl-2-Pyridyl)-1,2,4-Triazine-P,P'-Disulfonic Acid, 2NA Salt; Trans-4-(4-Dibutylamino)Styryl)-1-(3-Sulfopropyl)Pyr Oh/Inner Salt H2O; 1-Octadecylpyridinium P-Toluenesulfonate; Acid Yellow 29; 4-(5-Oxo-3-Pentadecyl-2-Pyrazolin-1-Yl) Benzenesulfonic Acid, Sodium Salt; Direct Orange 31; Sephadex-Sp-C-50, Ion Exchange Resin; 4-(4-(2-Hexadecyloxyphenyl)-5-Oxo-2-Pyrazolin-1-Yl) Benzenesulfonic Acid Sodium; Acid Yellow 42; Carboxy-Hexadecyloxybenzenesulfonic Methyl-Sulfophenyl-Thiadiazolinylidenehydraz; 2,4-Bis(5,6(4-Sulfophenyl)-1,2, 4-Triazine-3-Yl)Pyridine 4NA Salt H2O; Acid Orange 63; Reaactive Blue 15; Sephadex-Sp-C-25, Ion-Exchange Resin; 8-Quinolinesulfonic Acid; 8-Ethoxy-5-Quinolinesulfonic Acid, Sodium Salt Hydrate; 2-Mercaptobenzothiazole-5-Sulfonic Acid, Sodium Salt;

8-Hydroxyquinoline-5-Sulfonic Acid Monohydrate; 8-Ethoxy-5-Quinolinesulfonic Acid; Benzothiazole-2,5-Disulfonic Acid; N-(Methylsulfonyloxy)-Phthalimide; 6-Methoxy-3-(3-Sulfopropyl)-3H-Benzothiazolin-2-One Hydrazone; 2-Benzofuransolfonic Acid; 1,3-Dioxo-2-Isoindoleneethanesulfonic Acid, Potassium Salt; 4-Sulfo-1, 8-Naphthalic Anhydride, Potassium Salt, Tech.; 2-Methylthio-5-Benzothiazolesulfonic Acid; Indole-3-Acetaldeyde Sodium Bisulfite Addition Compound; 8-Bromo-2-Dibenzo-Furansulfonic Acid, Sodium Salt; 2-Methylthiobenzimidazolesulfonic Acid; 3-Methyl-2-Methylthio-6-Nitro-5-Sulfobenzothiazolium Methyl Sulfate; 8-(Chloromercuri)-2-Dibenzofuransulfonic Acid, Sodium Salt; 2-(3-Methly-2-Benzothiazolinyidene)-1-Hydrazinesulfonic Acid; 8=Sulfo-2,4-Quinolinedicarboxylic Acid; 8-Nitro-2-Dibenzofuransulfonic Acid; 8-Hyroxy-7-Iodo-5-Quinoliinesulfonic Acid; 6-Norharmansulfonic Acid; 4-Amino-3,6-Disulfo-1,8-Naphthalic Anhydride Dipotassium Salt; Harman-N-Sulfonic Acid; Indigo Carmine, Certified; 4-Dibenzofuransulfonic Acid, Sodium Salt Monohyrdate; 4-(2-Benzimidazolyl)-Benzenesulfonic Acid; Potassium Indigotrisulfonate; 2-Dibenzofuransulfonic Acid; Lucifer Yellow CH, Dipotassium Salt; Potassium Indigotetrasulfonate; 2-Dibenzofuransulfonic Acid, Sodium Salt; Lucifer Yellow CH; 7-Anilino-1-Naphthol-3-Sulfonic Acid; 2,8-Dibenzofurandisulfinic Acid, Disodium salt; Harmine-N-Sulfonic Acid, Sodium Salt; 2,3-Dimethyl-6-Nitrobenzothiazolium Para-Toluenesulfonate; 4,6-Dibenzofurandisulfonic Acid; 3-(3-Sulfooxypropyl)-2,5,6-Trimethylbenzothiasolium Hydroxide, Inner Salt; 3-Methly-2-(Methylthio)Benzothizolium P-Toluenesulfonate); 2,8, Dibenzofurandisulfonic Acid, Disodium Salt; 1-Ethyl-2-Methly-3-(3-Sulfooxypropyl)-Benzimidazolium Hydroxide, Inner Salt; Methanesulfonic Acid (1-Methly-2-Phenyl-6-Sulfo-4(1H)-Quinolyidene)Hydrazide; 2-Sulfothianthrene-5,5,10,10-Tetraoxide, Sodium Salt; 4-(4-Quinolylazo) Benzenesulfonic Acid; and 2-(Methylthio)Benzothiazole Ethyl P-Toluenesulfonate. All of the chemicals listed above are available from Aldrich Chemical Company (Milwaukee, Wis.)

Of the above listings, it is likely that the preferred processes will utilize a simple anhydride to soften the cornea, i.e. glutaric anhydride, succinic anhydride or maleic anhydride since each of these anhydrides hydrolyze into rather innocuous compounds.

Apparatus for Application of the Chemical Agents to the Cornea

Figure 1:
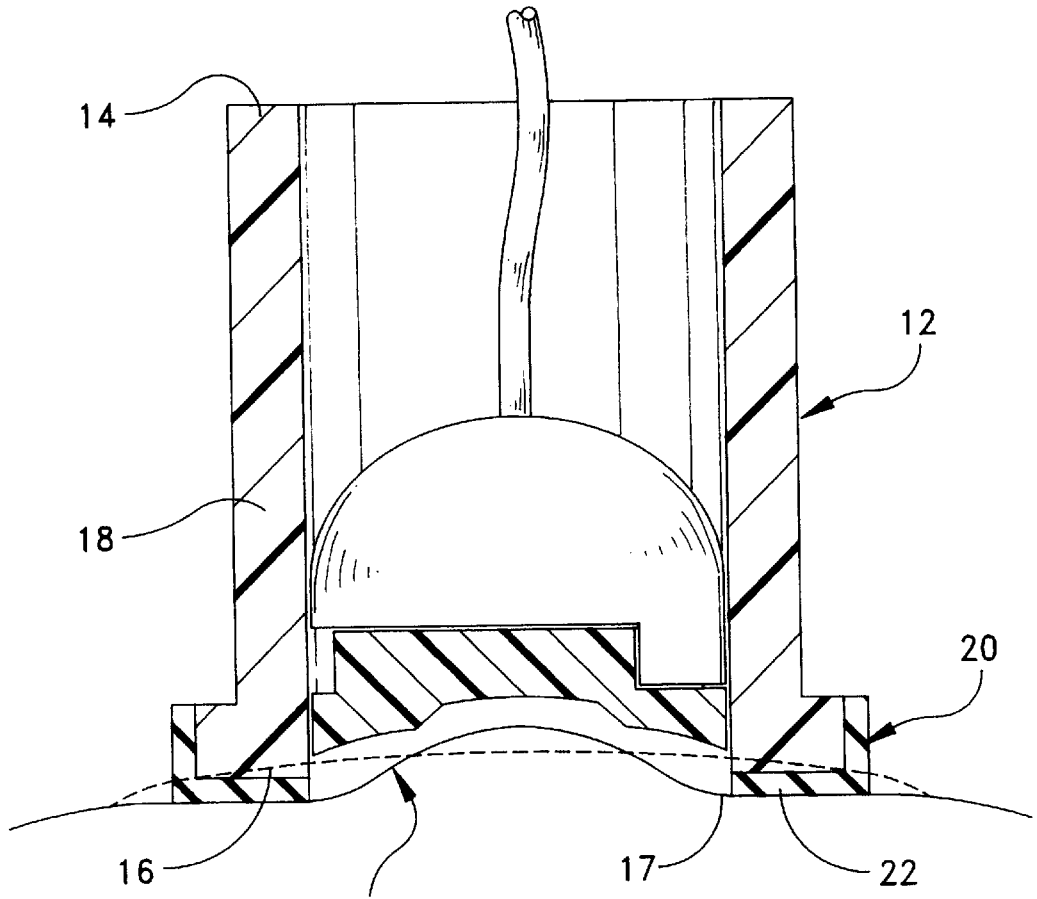
FIG. 1 is a cross-sectional view of a cornea undergoing treatment according to the teachings of the present invention.
Figure 2:
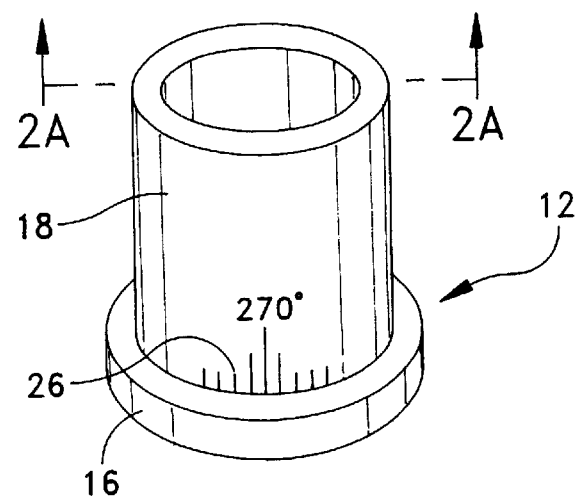
FIG. 2 is a perspective view of a staging device.
Figure 2A:
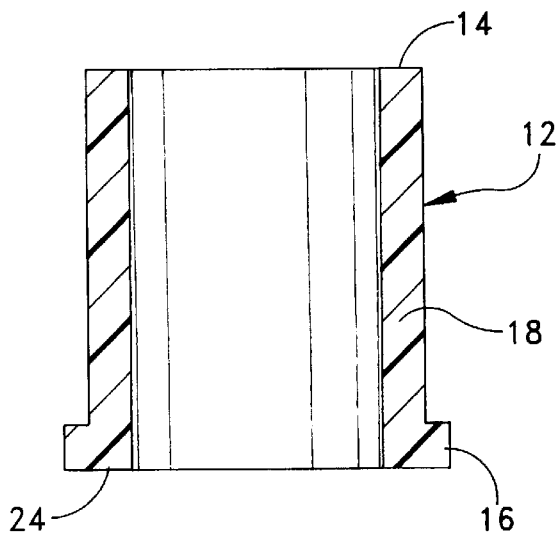
FIG. 2A is a cross-sectional view of the staging device as taken along line 2A—2A of FIG. 2.

Because it is desired to limit chemical exposure to only the corneal tissues 10 of the eye, a staging device generally indicated at 12 has been developed to limit the spreading of the liquid treatment solutions which will be topically applied to the cornea. Referring to FIGS. 2, 2A, and 2B, the staging device 12 is preferably cylindrical in shape having upper and lower ends, 14, 16 respectively, and is preferably manufactured from a plastic material by injection molding. However, the staging device 12 could also be formed from metal or fiberglass or any other suitable material. The staging device 12 is preferably 1.5 to 2.0 inches in height measured between the upper and lower ends 14, 16, and has an outer diameter at the lower end 16 of between 10–15 mm. As will be noted by those skilled in the art, the outer diameter of the lower end generally corresponds to the diameter of the outer limbic area 17 of the cornea 10 upon which the staging device 12 will rest when in use. The side wall 18 of the staging device 12 is preferably between 0.5–2.0 mm thick. The idea is for the staging device to sit directly on the limbic area to prevent leakage of the drug solutions beyond the treated surface of the cornea 10 (See FIG. 9). The staging device 12 further preferably includes an annular elastomeric gasket 20 (FIG. 2B) which is received around the lower end 16 of the staging device 12. The elastomeric gasket 20 can be formed from a variety of non-porous elastomeric materials, such as synthetic and natural rubbers, non-porous foams, closed cell sponge, etc. A downwardly facing portion 22 of the gasket 20 will engage with the surface of the limbic area 17 of the cornea 10 when positioned to form an annular seal with the surface of the cornea 10. It is contemplated that the lower edges 24 of the lower end 16 of the staging device 12 could be tapered slightly inwardly to better conform to the sloping surface of the cornea 10. Likewise, the downwardly facing surfaces 22 of the gasket 20 could also be tapered inwardly to provide a better fit against the surface of the cornea.

The staging apparatus 12 will be used for drug delivery to the cornea 10 as well as to guide and position the molds during reshaping. All drugs or solutions used in the methods are administered into the inside of the staging apparatus 12 after placement onto the cornea 10 wherein the interface of the gasket 20 with the cornea surface seals off the leakage of the solution from inside the device 12. To rigidly position the staging device 12 onto the cornea 10, as well as to prevent rotation thereof, a biological sealant or glue (not shown) may be applied to the downwardly facing portion 22 of the gasket 20 to adhere the gasket 20 to the limbic area 17 of the cornea 10. Any of the presently known biological sealants or glues would be acceptable in this context. Once the staging device 12 is in place, the gasket 20 forms a seal and prevents the leakage of solutions which are administered into the center of the staging device. In this manner, the solutions and drugs are applied only to the central area of the cornea 10 which is to be reshaped.

Figure 2C:
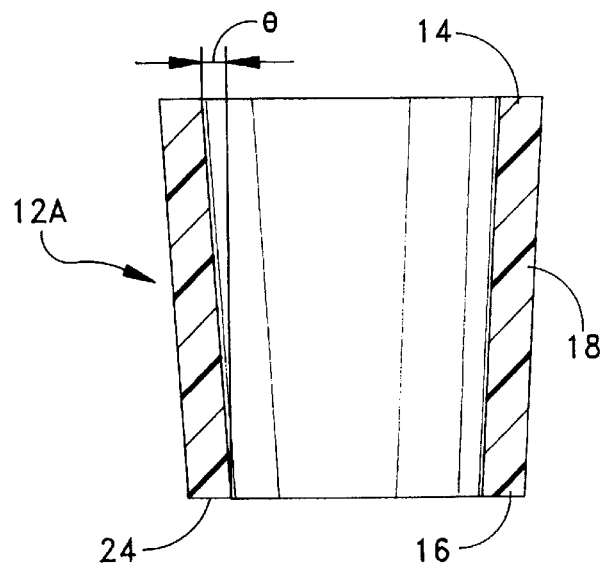
FIG. 2C is a cross-sectional view of a third embodiment of the staging device.
Figure 2B:
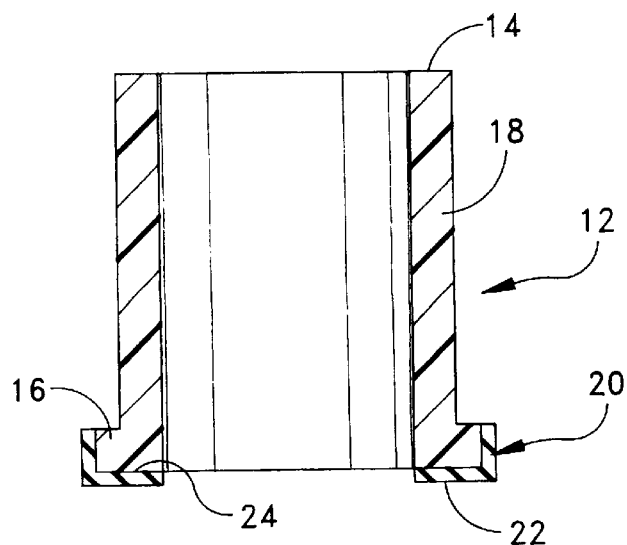
FIG. 2B is a cross-sectional view of a second embodiment of the staging device including a gasket thereon.

Although the preferred embodiment of the staging apparatus 12 is cylindrical it is also contemplated that an alternate staging apparatus 12A could have a wider diameter at the upper end 14 wherein the outer diameter thereof ranges from 15–35 mm (See FIG. 2C.)

It is also contemplated that the staging device 12 will have exterior markings 26 (FIG. 2) which will allow proper rotational alignment of the staging device 12 with respect to the eye, and also proper rotational alignment of the mold within the staging device for correction of astigmatism errors.

Removing Solutions from the Staging Device

Figure 3:
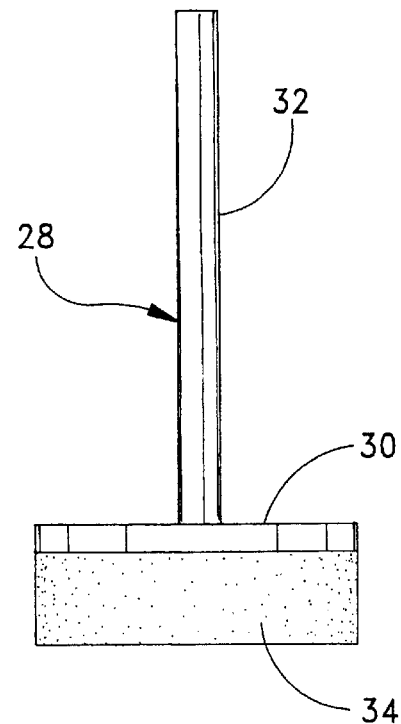
FIG. 3 is an elevational view of the sponge assembly.

Since the staging device 12 will effectively retain all of the drug solutions within its interior, it will be necessary to selectively remove the solutions during the procedure. For example, it will be necessary to wash the cornea 10 with various buffer solutions, and to apply different drug solutions at different times during the procedure. For this purpose, the Applicants have developed a simple sponge absorbing device (FIG. 3) generally indicated at 28 comprising a planar disc 30 having a handle portion 32 extending outwardly from an upper side thereof. The disc 32 has an outer diameter which will allow insertion of the disc 32 into the interior of the staging device 12. An absorbent sponge material 34 is adhered to the lower side of the disc 30 so that the sponge material 34 engages with the surface of the cornea 10 to absorb any solution within the staging device 12 (See also FIG. 10).

Reshaping

Figure 4:
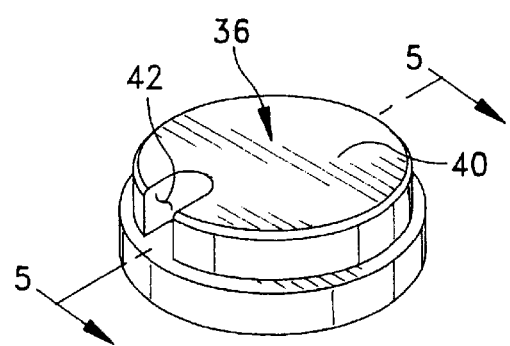
FIG. 4 is a perspective view of a mold as used in the method of the present invention.
Figure 5:
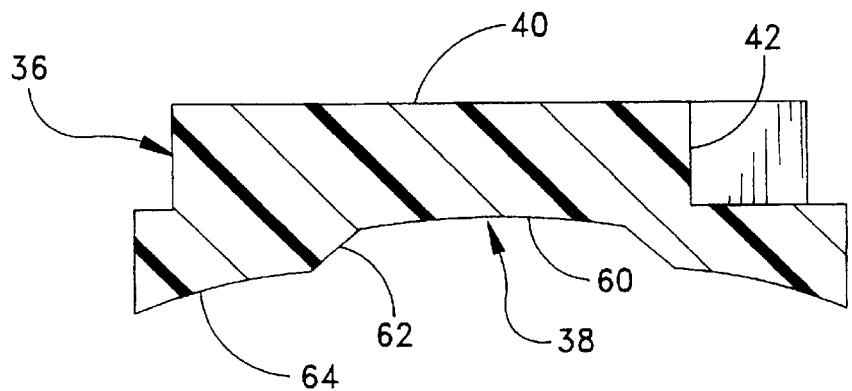
FIG. 5 is a cross-sectional view of the mold as taken along line 5—5 of FIG. 4.

After the cornea 10 is treated with a chemical softening agent, a mold generally indicated at 36 of predetermined curvature and configuration is fitted into the staging device (See FIGS. 4–5, and 11–12). Turning to FIGS. 4–5, the mold 36 is preferably cylindrical in shape having a mold surface generally indicated at 38 which will engage the anterior surface of the cornea 10, and further having an opposing rear surface 40. The mold 36 can be fabricated from any one of a variety of materials, including metal, glass, plastic, quartz, or epoxy materials. With regard to preferred materials for fabrication, and as will be described hereinafter in Example 1, the present preferred method for restabilizing the cornea 10 after shaping is by means of exposure to UV light. It is thus preferred that the mold 36 be fabricated from a UV permeable plastic, such as polymethyl methacrylate. This plastic material can first be molded in a generic mold shape and then have the mold surface 38 cut to a predetermined shape by a lathe.

The mold surface 38 is provided with a predetermined geometric configuration which, when engaged with the surface of the cornea 10, is intended to reshape the cornea to an emmetropic configuration. The specifics of the geometric curvature of various portions of the mold surface 38 will be discussed hereinafter. The mold surface 38 can be formed by any one of a variety of known methods for forming optical lenses such as lath cutting, molding or milling depending on the fabrication material of the mold 36.

Figure 6:
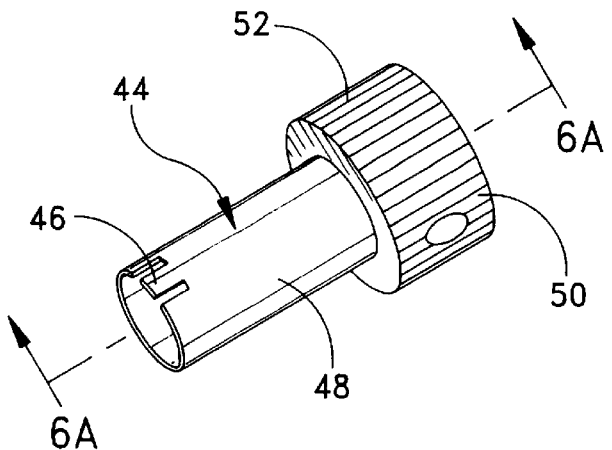
FIG. 6 is a perspective view of a mold holder for use in the method of the present invention.
Figure 6A:
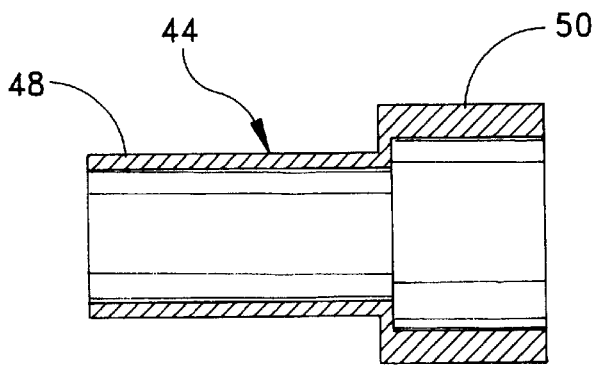
FIG. 6A is a cross-sectional view thereof as taken along line 6A—6A of FIG. 6.
Figure 7:
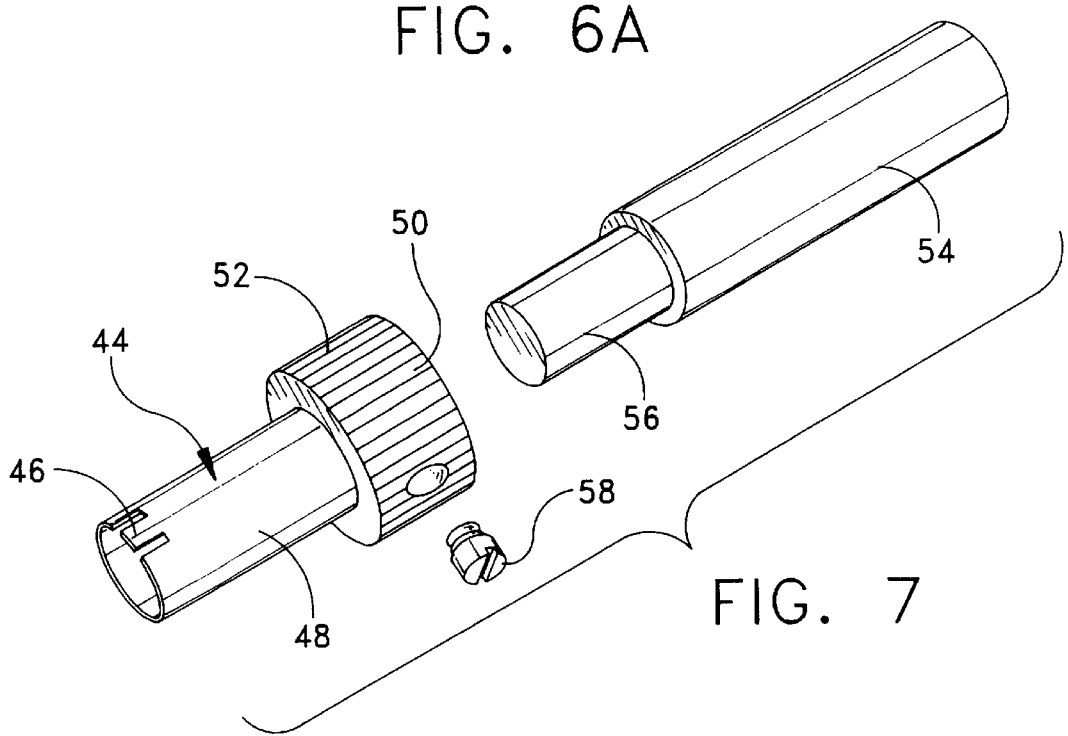
FIG. 7 is a perspective view of the mold holder and a handle which can be attached to the mold holder.

The rear surface 49 of the mold 36 is preferably provided with a key 42 so that the mold 36 can be properly rotationally oriented on the surface of the cornea 10. Rotation of the mold 36 can be accomplished by a holder tool generally indicated at 44 having a complementary detent 46 on the end thereof (FIGS. 6 and 6A). More specifically, the holder tool 44 has a hollow cylindrical body portion 48 which is intended to be inserted into the staging device to engage the mold 36 situated threin. The detent 46 is located at the distal end of the body portion. At the proximal end of the body portion 48 there is an enlarged diameter finger grip 50 having a fluted outer surface 52 which can be easily grasped and rotated by the surgeon. The finger grip is also hollow to provide a continuous open through the tool holder 44. Referring to FIG. 7, holder 44 is shown in conjunction with the end of a light rod 54 which will be used to apply light through the mold 36. One end of the light guide 54 is provided with a reduced diameter portion 56 which fits into the open end of the finger grip 50 of the holder tool 44. The light guide 54 is maintained in assembled relation with the holder tool 44 by means a set screw 58 which extends through the finger grip 50 and engages with the reduced diameter end 56 of the light guide 54.

After the mold 36 is oriented in the staging device 12, downward pressure is applied to the mold 36 for a predetermined period of time (1–10 minutes) to re-shape the softened cornea 10. Pressure is preferably applied by pressing downwardly on the holder tool 44 which is engaged with the mold 36 (See FIG. 12).

Mold Configurations

Various types of mold configurations can be used to treat different refractive errors of the eye. Hereinbelow, the Applicant's will discuss various mold configurations which can be utilized in the subject process.

A. Residual Astigmatism (Internal Astigmatism)

Internal astigmatism is the astigmatism in the eyes optical system other than that measured on the corneal surface. A patient with internal astigmatism will require a toric central curve mold application. When the spectacle refractive astigmatism equals the corneal astigmatism in a given median, the internal astigmatism is zero. This is to say that the total astigmatism of the eye is produced by the corneal toricity. Sphericalizing the cornea with a mold of the subject invention will result in zero refractive astigmatism.

If the refractive astigmatism differs in magnitude but the same direction as the corneal toricity, the difference is the internal astigmatism. There are two cases. One where the corneal astigmatism is greater than the refractive astigmatism, where a bitoric mold would be used having its steeper curve aligned with the steeper corneal meridian. The resultant optical outcome would be an emmetropic with a toric cornea (the axis of corneal astigmatism would be the same pre-post procedure.) The other case would be a corneal astigmatism of less magnitude than the refractive astigmatism along the same meridian. The mold for treating this condition would have a bitoric central curve. Axis of astigmatism mold correction 90° from the refractive astigmatism axis. The mold would have a toric power equal to the difference between the power of the refraction and corneal astigmatism. The resultant optical outcome would be an emmetropic eye with a toric cornea.

EXAMPLE A

Corneal K's 44/46 at 90 (s diopter of corneal astigmatism)

Spectacle refraction −300=−100×180 (1 diopter refractive astigmatism)

Mold toricity −100×180

EXAMPLE B

Corneal k's 44/45 at 90 (1 diopter of stigmatism)

Spectacle refraction −300=−200×180 (2 diopter of astigmatism)

Mold toricity −100×90

The visual optics are fundamental for those skilled in the art. The resultant internal astigmatism as defined by the formulas will be corrected for with a bitoric mold having an axis of myopic correction with the axis of residual myopic astigmatism.

Where the axis of corneal astigmatism and the axis of spectacle refraction are not along the same meridian, a new bitoric mold axis and power can be determined by applying visual optics formulas known in the art.

The spherical mold is fit flatter than the corneal astigmatic meridian by the magnitude of the spectacle refraction. The mold should have a power equal to the power of the flat corneal astigmatic meridian with a refractive power along that meridian. This method works only if there is no residual astigmatism.

When a residual astigmatism exists, a bitoric mold is used which has a minus cylinder axis at the same axis as the residual astigmatism. The power difference between bitoric curves is equal to the magnitude of the residual astigmatism. The spherical component of the mold is determined by the aforementioned method.

B. Spherical Base Curves for Mold Design

The spherical mold is fit flatter than the flat corneal astigmatic meridian by the magnitude of the spectacle refraction along that flat meridian. The mold base curve should have a power equal to the power of the flat corneal astigmatic meridian minus the refractive power along that meridian. This method works only if there is no residual astigmatism.

(1) Simple Myopia a. −300 sph spectacle refraction b. 44 sph corneal power c. 44−3=41 diopters=mold base curve power (2) Simple Astigmatism a. p1=−100×180 b. 43/44 at 90 corneal powers c. 44 (flat corneal power)−plane (0)=44 diopter mold base curve power. The mold is aligned on the flat corneal meridian (3) Compound Myopic Astigmatism a. −200=−100×180 b. 43/44 at 90 corneal powers c. 44−43=1 diopters=mold base curve power

C. Base Curve Mold Configuration for Hyperopia, Compound Hyperopic Astigmatism, and Presbyopia are Computed Using the Same Formulas The base curve of the mold is steeper than the flat corneal meridian by the magnitude of the spectacle refraction along that flat corneal meridian. The base curve can be spherical or aspherical or bitoric and the optic zone diameter will vary depending on the magnitude of the power correction required. The mid-peripheral curve will be flatter, preferably aspherical, but may be spherical and will in general be flatter and wider as the central refractive power/corneal power ratio increases. This is to say that the more hyperopic refractive correction, the steeper the central base curve and the flatter the mid-peripheral curve becomes.

The concept of the mold (for all refractive errors) is to reconfigure a given square mm surface area of the cornea by flattening the optic zone (in myopes) and displacing the tissue laterally into the relief zone pocket, without changing the overall square mm surface area of the cornea.

The overall configuration is a smooth spherical optic zone (unless a bitoric curve is necessary for residual astigmatism) with a gradual relief zone that gradually flattens out to the natural peripheral corneal curvature.

Mold Dimensions

Referring to FIGS. 5 and 8C, there is shown a mold configuration 36 of the general type which will be used in the processes of the present invention. The mold 36 is particularly suited for treating a myopic cornea wherein the object is to flatten out the central portion of the cornea 10. In this regard, the mold surface 38 includes a central curve zone 60, a single mid-peripheral (relief) curve 62, and a large base curve 64. The width of the central curve 60 is about 4 mm, and the width of the mid-peripheral (relief) curve 62 is between 1 mm and 1.5 mm, spherical or aspherical. The configuration of the base curve was discussed generally hereinabove. The mid-peripheral curve 62 is 2–15 diopters steeper than the central base curve 60 for myopic corrections. The larger the base curve/k relationship (increased myopia, the steeper and wider the mid-peripheral (relief) curve 62. The same holds true for hyperopia wherein the rule is that the larger the base curve/k relationship, the flatter and wider the mid-peripheral curve 62. The mid-peripheral curve 62 in hyperopic molds are between 2–15 diopters flatter than the central base curve 60.

The type and magnitude of corneal astigmatism will influence the width and curvature of the mid-peripheral (relief) curve 62 in this and likely all mold designs. Larger magnitudes of compound hyperopic astigmatism (CHA) will require flatter and wider mid-peripheral curves and larger magnitudes of CMA will require steeper and wider relief mid-peripheral curves. Small degrees of total corneal astigmatism and small spherical emmetropics will require less of a difference in curvature between the central base curve and mid-peripheral relief curve. Aspheric mid-peripheral curves will optimally be used for astigmatic corneas with reverse geometry mold designs. If an outer peripheral curve is utilized in the mold, it should have a width of about 0.25 mm–2.0 mm. The curvature of the peripheral curve is somewhere near cornea alignment.

Referring now to FIGS. 8A–8B, a mold 36A incorporating multiple mid-peripheral curves is shown. The width of the central curve 66 is between about 4–9 mm. The configuration of the central base curvature was discussed generaly hereinabove. The first mid-peripheral relief curve 68 (innermost curve) has a diameter of 0.3 mm to about 4.0 mm. This curve is 3–9 diopters steeper than the central optic zone 66. The second mid-peripheral relief curve 70 has a width of 0.3–1.5 mm and is flatter than the first relief curve 68. If an outer peripheral curve 72 is used, it should have a width of between about 0.25 mm and 1.0 mm. This peripheral curve 72 is nearer to the corneal alignment than the first mid-peripheral relief curve. The function of the peripheral curve 72 is to block the cornea from structural flow outside of the periphery of the mold 36A.

Figure 8D:
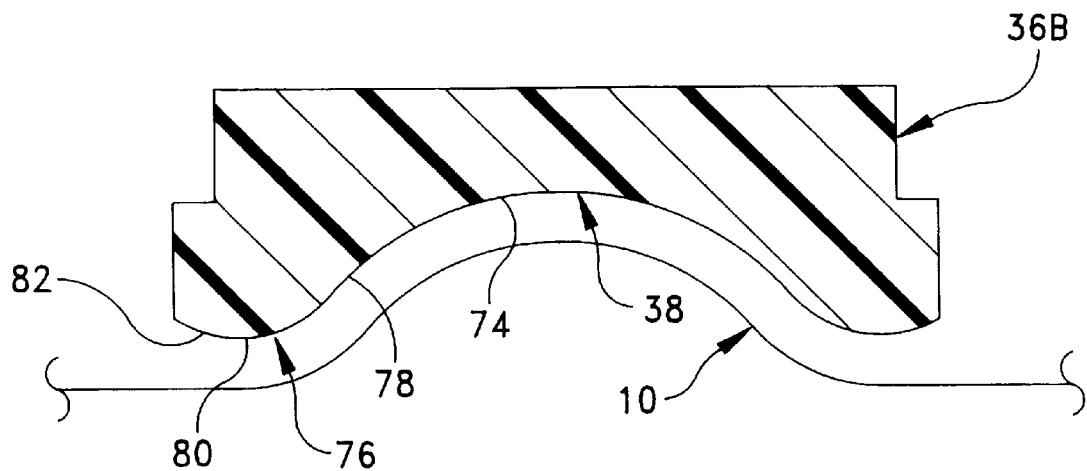
FIG. 8D is a cross-section view of a mold for use in hyperopic and compound hyperopic astigmatism patients.

Referring now to FIG. 8D, a mold 36B for use in treating hyperopic and compound hyperopic astigmatism is illustrated. The mold 36B is first divided into two zone, a central optic zone 74, and a mid-peripheral zone generally indicated at 76. The mid-peripheral zone is divided into three separate curvatures areas, namely a transition zone 78, an apex 80 of the mid-peripheral curvature 76 and an outer curve portion 82. Generally speaking, the central optic zone 74 is steeper than the corneal curvature (spherical, aspherical or bitoric). The transition zone 78 is flatter than the optical zone 74, but not as flat as the apex zone 80. The apex 80 of the mid-peripheral curvature 76 bears on the corneal surface and may move laterally or medially on the curvature zone 76. The outer curve 82 is stepper than the apex area curve 80 and aligned more with the surface of the cornea 10.

Figure 8E:
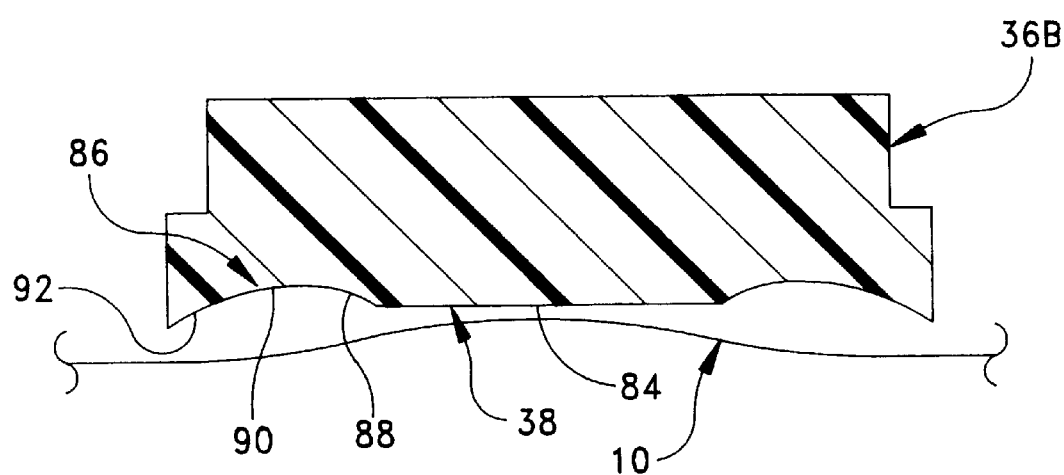
FIG. 8E is a cross-sectional view of yet another mold configuration.

Referring to FIG. 8E, yet another mold configuration 36C is illustrated for use in treating myopia or mixed myopic astigmatism. The mold surface 38 is provided with a central optic curve zone 84, and a mid-peripheral relief zone generally indicated at 86. The central optic curve zone 84 can be spherical, aspherical or bitoric, and is approximately 6.0–10 mm is diameter, with an optimal diameter of about 7 mm. The relief zone 86 is preferably divided into three areas, namely, an inner portion 88, an apex portion 90 and outer peripheral portion 92. The mid-peripheral relief zone 86 is a concave surface which is approximately 1.5–3.0 mm in width having a variable apex location within the curve 86. The inner portion 88 of the mid-peripheral relief curve 86 is preferably flatter than the optical zone 84 (spherical or aspherical). The apex portion 90 of the relief curve 86 is approximately 0.3–0.4 mm in width and the apex thereof may be skewed to medial or lateral locations of the relief curve 86. The outer peripheral portion 92 of the relief curve 86 is approximately 0.25–1.5 mm in width, and maybe steeper than the optical zone 84 and also steeper than the corneal curvature under the mold 36 at that location. The radius of curvature of each of the portions of the mid-peripheral relief zone 86 is off alignment with the line of sight. The preferred embodiment of the mold 36C will not have an outer peripheral curve zone 92.

All of the above-described mold information is of the general type known in the art of fitting orthokeratology contact lenses. The information has been provided as a means for explanation of the various molds used during the processes described, but it is not intended to limit the scope of the disclosure to any particular type or design of mold structure as many different mold design will work to produce the same effect of shaping the corneal tissues to the curvature of the mold to alter the refractive power of the eye.

Stabilization of the Cornea After Shaping

The last and most crucial step in the process comprises restabilizing the corneal tissues after reshaping into the new "emmetropic" configuration. For purposes of the present disclosure the Applicant has adopted the term "stabilizing agent" as a means to refer to all of the potential agents for restabilizing the collagen matrix of the eye. Included among the stabling agents to be described hereinafter are chemical stabilizing agents, light energy including UV and visible light, thermal radiation, microwave energy, and radio waves.

Crosslinking Using UV Light

It is well known that UV radiation and UVC is effective in crosslinking collagen. (See the to Kelman and DeVore U.S. Pat. Nos. 4,969,912; 5,201,764; 5,219,895; 5,354,336; and 5,492,135 regarding UV crosslinking of collagen materials). While the exact mechanism is not well understood, it is thought that UVC acts primarily on tyrosine residues in the collagen molecule. Accordingly, the polymerization or crosslinking of the reshaped corneal tissues may be carried out simply by exposing the cornea to short wave UV light (e.g. 254 nm). However, the rate of polymerization is not practical for use because of the potential damage to the corneal tissues caused by long term exposures to UV light. The rate of polymerization may be significantly increased by applying appropriate redox initiators to the cornea prior to the UV light exposure. Without such an initiator, UV polymerization, would require at least 10 minutes of exposure.

Suitable, but non-limiting, examples of some initiators include sodium persulfate, sodium thiosulfate, ferrous chloride tetrahydrate, sodium bisulfate, and oxidative enzymes such as peroxidase or catechol oxidase.

A suitable dosage of the chemical initiator is one that sufficiently promoted the polymerization of the corneal matrix within between about 30 seconds and about 2 minutes, preferably between about 30 second and 1 minute, but insufficient to cause oxidative damage to the corneal tissues.

Polymerization by UV irradiation may be accomplished in the short wave length range by using a standard 254 nm source of between about 4 and 12 watts. Polymerization generally occurs in between about 30 seconds and about two minutes, preferably no longer than 1 minute, at an exposure distance of between about 1.5 and 5 cm distance. Because excess UV exposure will begin to depolymerize the collagen polymers ad cause eye damage, it is important to limit UV irradiation for short periods. At 254 nm, the penetration depth is very limited.

While short wave UV in the range of 254 nm is disclosed, it is to be understood that other wavelengths of UV would also be suitable depending on application of a suitable photoinitiator matched to the particular wavelength. In the experiments outlined below, the UV exposure was conducted with no filter, thereby providing broadband UV irradiation. Filters will provide a more specific wavelength, which will be matched to an appropriate photochemical or redox initiator. Filters also reduce the temperature elevation at the exposure site. Sodium persulfate which is listed as the preferred initiator in Example 1 exhibits a maximum absorption at 254 nm, but appears to be effective at much higher wavelengths. For maximum efficiency, it is preferred to match the UV wavelength to a specific redox or photochemical initiator.

Gamma Irradiation

Polymerization, or crosslinking, can also be accomplished using Gamma irradiation between 0.5 to 2.5 Mrads. However, excess Gamma exposure will also depolymerize collagen polymers.

Chemical Crosslinking

There are many potential chemical "stabilizing" agents for use in chemically cross-linking the collagen matrix.

The historical collagen cross-linking technique utilizes glutaraldehyde. Glutaraldehyde and other aldehydes, such as glyoxal, acrolein, acetaldehyde, butyraldehyde, propionaldehyde, and formaldehyde create lateral bridges between polypeptide chains and between collagen fibers. Other suitable, but non-limiting, chemical cross-linkers include periodates, acyl azides, Denacol® ethers, i.e. Sorbitol Polyglycidyl Ether, Polyglycerol Polyglycidyl Ether, Pentaerythritol Polyglycidyl Ether, Diglycerol Polyglycidyl Ether, Triglycidyl Tris Isocyanurate and Glycerol Polyglycidyl Ether, bifunctional acylation agents, including anhydrides, acid chlorides, and sulfonyl chlorides, e.g. 1,2, 3,4-cyclobutanetetracarboxylic dianhydride, Tetrahydrofuran-2,3,4,5-tetracarboxylic dianhydride, 1,2,4, 5-benzenetetracarboxylic di-anhydride, ethylenediaminetetraacetic dianhydride, bicyclo(2,2,2)oct-7-ene-2,3,5,6-tetracarboxylic dianhydride, glutaryl dichloride, adipoyl chloride, 3-methyladipoyl chloride, pimeloyl chloride, terephthaloyl chloride, isophthaloyol dichloride, phthaloyl dichloride, 1,4-phenylene bis(chloroformate), 2,4-mesitylenedisulfonyl chloride, 2,6 naphthalenedisulfonyl chloride, malonyl dichloride, and homobifunctional amine cross-reactive cross-linkers such as homobifunctional imidoesters and homobifunctional N-hydroxysuccinimidyl are also suitable.

Unfortunately, many of these agent elicit adverse tissue reactions, and therefore their use must be carefully controlled and directed to a specific site. In this regard, chemical cross-linking is not discussed herein as the preferred method of stabilization. However, such agents would be highly useful in the present method should appropriate delivery systems become available in the future.

Thermal Radiation

Heat is another possible means of cross-linking, or "stabilizing" the corneal tissues after reshaping. It is generally known that the application of heat speeds up tissue metabolism and will help stabilize the tissue faster than if no heat were applied. Laser thermal keratoplasty (LTK) is the use of heat produced at specified points in the cornea stroma by absorption of laser light to modify the structure and mechanical properties of stromal collagen. Typically, in LTK, the laser is directed to a particular spot on the eye. As the spot absorbs light and heat up to about 55–60 degrees centigrade, the collagen will shrink. Rings of spots are used to tighten the tissues to create a change in the anterior curvature of the cornea. As a final step in the present methodology, the reshaped cornea could be exposed to laser light wherein the corneal tissues would be heated and stabilized in the new emmetropic configuration. The treatment parameters at this point in development are purely speculative.

Microwave Energy

Microwave energy is also currently being investigated as a means of treating myopia. The treatment has been called microwave thermokeratoplasty, and has been previously documented by D. X. Pang, B. S. Trembly, L. R. Bartholomew, P. J. Hoopes, and D. G. Campbell, *Microwave Thermokeratoplasty*, Investigational Ophthamology and Visual Science, 36:s988, 1995, and D. X. Pang, B. S. Trembly, L. R. Bartholomew, and P. J. Hoopes, *Microwave Thermokeratoplasty: Reshaping Corneal Contour* (*Corneal Microwave-TKP*), Accepted for Publication, International Journal of Hyperkeratoplasty, (1998). See also U.S. Pat. No. 4,881,543 to Trembly entitled *Combined Microwave Heating and Surface Cooling of the Cornea* (1989), and U.S. Pat. No. 5,618,284 to Sand, *Collagen Treatment Apparatus*, (1997). The mechanism for cross-linking appears to be via the creation of heat at specific sites in the stroma. As stated above for thermal radiation, it is generally known that the application of heat speeds up tissue metabolism and will help stabilize the tissue faster than if no heat were applied. It is contemplated that microwave energy could be used to generate heat in the stroma to stabilize the corneal tissues after softening and molding as described in the present invention. As a final step in the present methodology, the reshaped cornea could be exposed to microwave energy wherein the corneal tissues would be heated, either at specific points or throughout the whole cornea, and stabilized in the new emmetropic configuration. The treatment parameters at this point in development are purely speculative.

Application of Heat Through the Mold

Another possible technique of applying heat to the cornea would be through direct contact with the mold. In this regard, the mold could be provided with a controlled heating element to heat the mold body to a predetermined temperature. Such heating could be accomplished by electric elements or by a heated fluid flow through the mold.

Radio Waves

It is still further contemplated that radio frequency energy could be used to generate heat in the stroma to stabilize the coreal tissues after softening and molding as described in the present invention. As a final step in the present methodology, the reshaped cornea could be exposed to radio frequency (RF) energy wherein the corneal tissues would be heated, either at specific points or throughout the whole cornea, and stabilized in the new emmetropic configuration. The treatment parameters at this point in development are purely speculative. See U.S. Pat. No. 5,638,384 to Gough et al entitled *Multiple antenna ablation apparatus*, (1997) describing the use of RF energy in surgical ablation techniques.

Visible Light

It is also possible to crosslink collagen using visible light. However, this method will require a photochemical initiator to transfer photoenergy into a free radical chemical reaction. Suitable, but non-limiting, photochemical dye initiators include Pheno-safranin, methyl red, bromphenol blue, crocein scarlet, phenol red, alcian blue, Rose Bengal, Methylene blue, A zure A, Toluidine blue, Eosin Y, Evans blue, Methylene green, Amythest violet, Lumazine, Thionine, Xanthopterin, 2,3,5-triphenyl-tetrazolium Cl., Acridine red, Acridine orange, Proflavine, Rosazurin, Azure B, Bindschedler's green, Primuline, Acridine yellow, Neutral red, Erythrosine, Fluorescein, Indo-oxine, and Malachite green. Of these chromophores, Fluorescein, Eosin, Indo-oxine and Rose bengal appear to be best suited for corneal use. It is noted that the exposure times for these chromophores are excessive and therefore, the use of these chemical may not be practical in actual usage. However, use is being tested for optimum performance times.

It is thought that Redox initiators will work much faster. Suitable but non-limiting, redox initiators include Diphenylamine, Erioglaucin A, 2,2'-Dipyridyl ferrous ion, and N-Phenylanthranilic acid.

Visible Light Stabilization Following Destabilization Using a Sulfonic Acid Chromophore An alternative technique for reshaping the cornea may comprise destabilizing the cornea with a sulfonic acid dye, followed by reshaping the cornea, and stabilizing the cornea by exposure to a specific wavelength of visible light corresponding to a maximum absorbance of the chromophore attached to amines reacted in the softening process.

Suitable, but non-limiting sulfonic acid dyes include: lucifer yellow vs, direct yellow 8, 2,2'-azinobis (3-ethylbenzothiazoline-6-sulfonic acid), 4,5-dihydroxy-3-(4-sulfo1napthylazo)27napthalenedisulfonic acid, 2-dibenzofuransulfonic acid, 1-(2-hydroxyethyl) quinolinium p-toluenesulfonate, brilliant sulphaflavine, thiazine red r, pyrogallol red, papaverine sulfonic acid, direct yellow 27, napthylazoxine a, 1-ethyl-2undecyl-5-benzamidazolesulfonic acid, hoechst 2495, 8-hydroxy-7-(4-sulfo-1-napthylazo)-5-quinolinesulfonic acid, 3-hydroxy-4 (2-hydroxy-4-sulfo-1-napthyl-azo)-2-napthalenecarboxylic acid, 1-hexadecanesulfonic (methyl-sulfobenzothiazolinylidene)hydrazid, sulfobromophthalein sodium hydrate, prmulin, sulforhodamine g, 8-hydroxy-5-(1-napthylazo)-2-naphthyalenesulfonic acid, 2-methylthio-3-phenylbenzothiazolium para-toluenesulfonate, 2-(m-aminophenyl)-1-dodecylbenzimidazole-5-sulfonic acid, 2-(4-bromobenzyl)isothiothiouronium 8-(4-hydroxy-1-naphthylazo)2naphthalenesulfonate, (hexadecyl-methylsulfamoyl)benzenesulfonic (me-sulfo-bz-thiazolinyliden)hydrazid, merocyanine 540, fast sulphon black f, 2-(3-amino-3-methylpentyl)-1-octadecyl-5-benzimidazolesulfonic acid, sulforhodamine b, 3,6-bis-(4-solfo-1-naphthylazo)-4,5-di-oh-2,7-naphthyalenedisulfonic acid, copper phthalocyanine-3,4',4",4$^{111}$-tetrasulfonic acid, 1-hexadecanesesulfonic acid, 4-(hexadecylsulfamoyl) bezenesulfonic acid, nickel phthalocyaninetetrasulfonic acid, azocarmine g, sulforhodamine 101 hydrate, 6,6'-(1,1'-biphenyl44'diylbisazo)bis (4amino5hydroxy13naphthalenedi-so3h2ona salt), azocarmine b, carboxy-hexadecyloxybenzenesulfonic acid, 1-hexadecanesesulfonic acid, thiazol yellow g, carboxy-hexadecylsulfonylbenzenesulfonic acid, 1-hexadecanesesulfonic acid, chlorazol azurine, 3-methyl-2-benzothiazolinone azine, methylthymol blue, reactive blue 15, acetamidohexadecylsulfonylbenzenesulfonic acid, owens blue, direct yellow 29, indocyanine green

EXAMPLE 1

Figure 9:
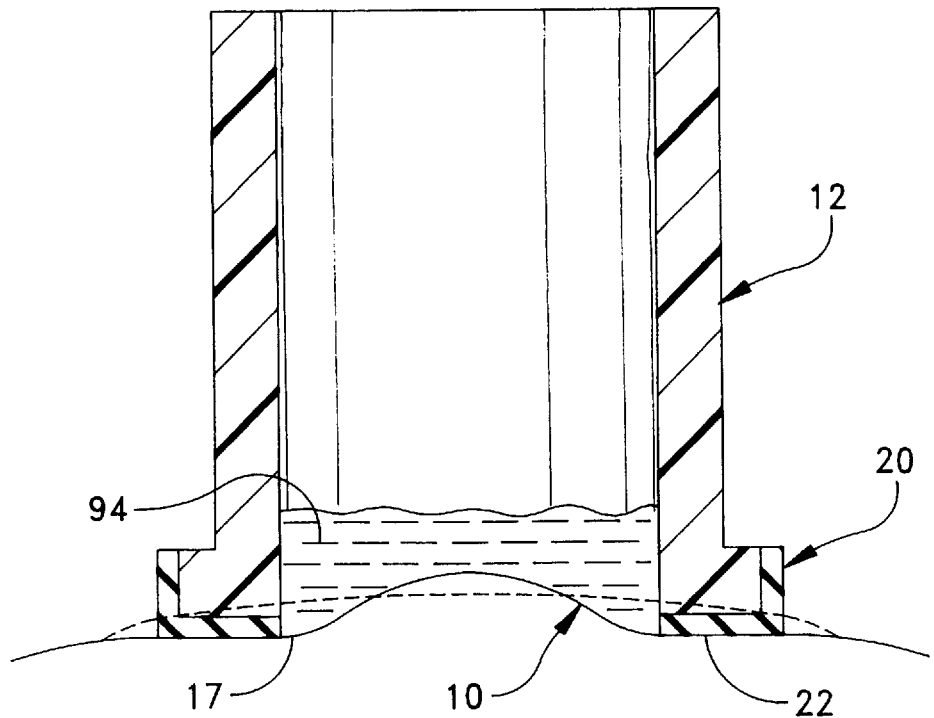
FIGS. 9–14 are cross-sectional views showing various stages of the method of the present invention.
Figure 10:
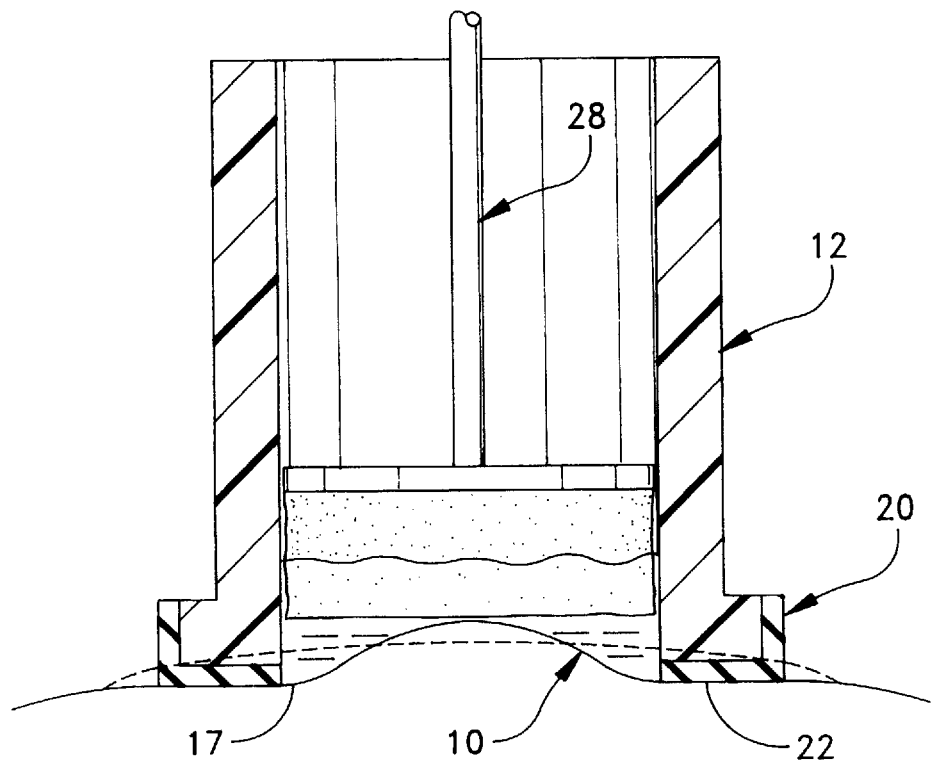
Figure 11:
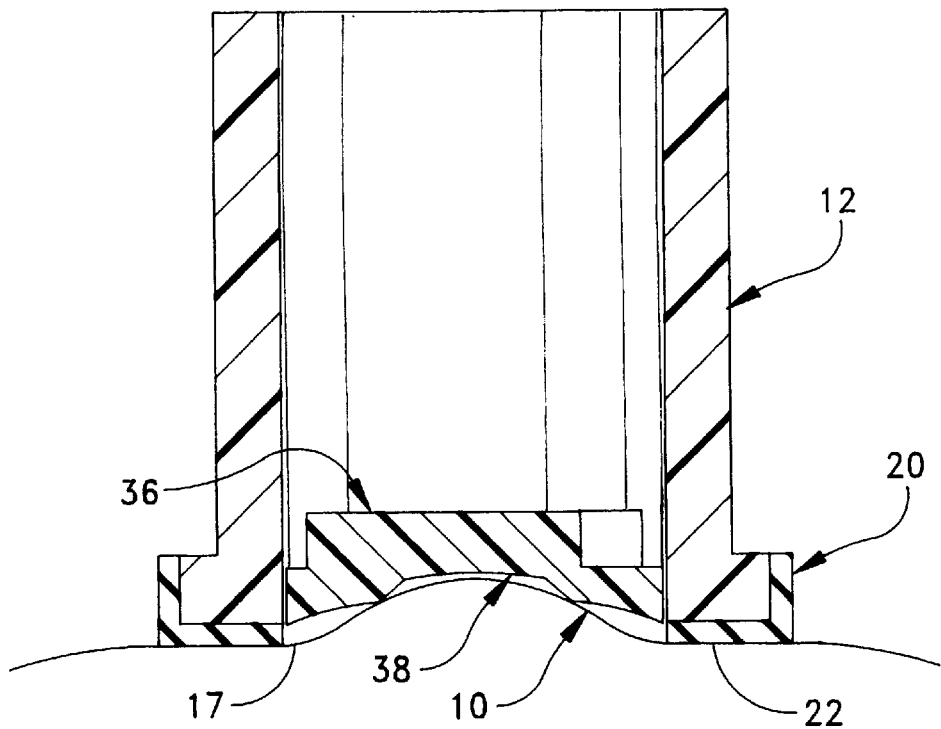
Figure 12:
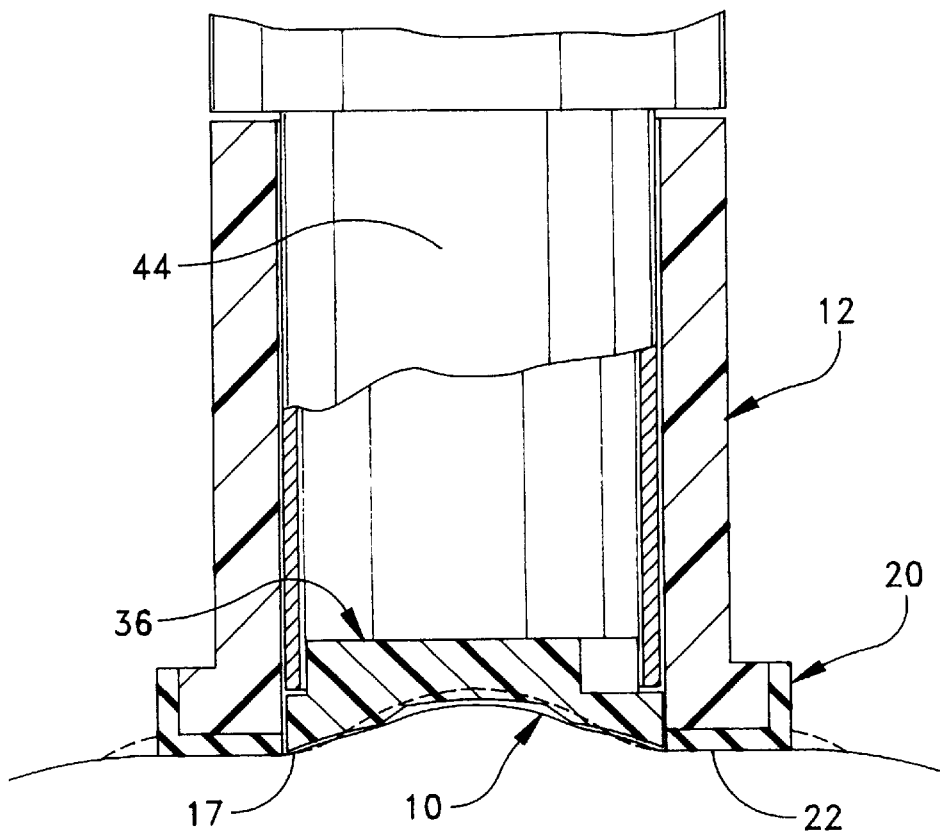
Figure 13:
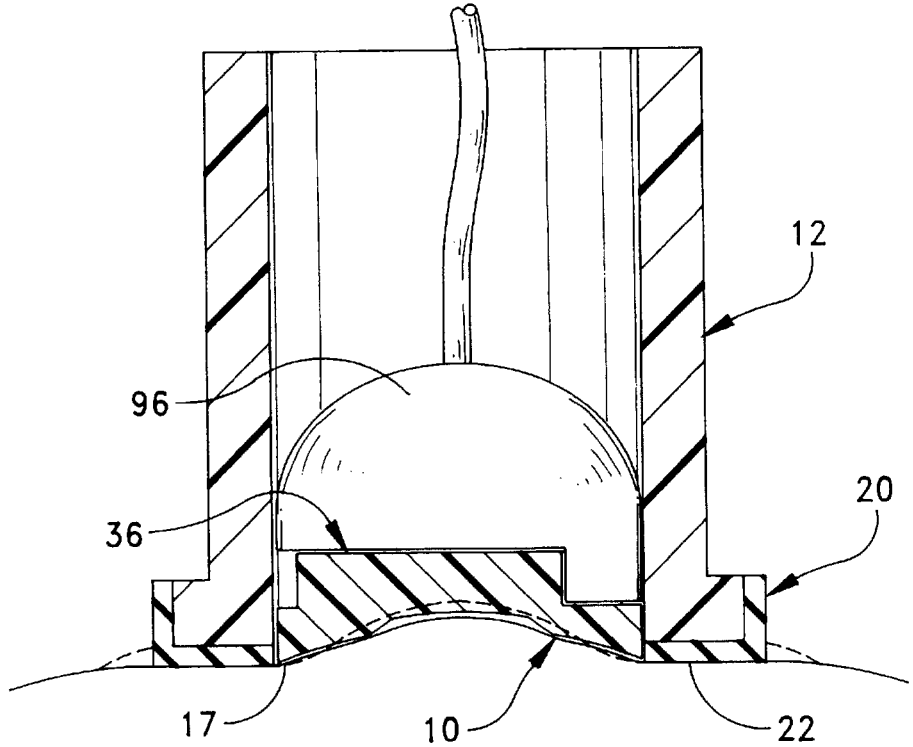

Preferred Methodology (1) Apply the staging apparatus 12 to the eye (FIG. 9);

(2) Pretreat the cornea (10—shown in solid line) with 0.02M disodium phosphate buffer solution (94), pH 8.5 for 1 minute (FIG. 9);

(3) Remove excess buffer (94) with the sponge apparatus (28) (See FIG. 10);

(4) Treat cornea (10) with a solution containing 5–50 mg of glutaric anhydride dissolved immediately before application in 1 ml of 0.02M disodium phosphate, pH 8.5. The preferred concentration of glutaric anhydride is 10–30 mg pre ml of disodium phosphate;

(5) Remove the anhydride solution with sponge apparatus;

(6) Place a shaping mold (36) into the staging apparatus 12, rotate to the desired position using the tool holder 44, and apply appropriate pressure to attain the desired anterior curvature of the cornea (10) (See FIG. 12) (the original corneal shape is now shown in broken line and the new second configuration is shown in solid line);

(7) With the mold 36 in place, treat the cornea with a Redox initiator in a slightly alkaline buffer. For sodium persulfate, preferably use 0.1M to 0.5M sodium persulfate in 0.02M phosphate buffer pH 8.0. The preferred concentration of sodium persulfate is 0.2M to 0.4M;

(8) With the mold 36 still in place, expose the corneal surface to UV irradiation in the 250–390 nm range. Preferably an EFOS Novacure unit is utilized and set at 3000 mW/cm$^2$ for 10–120 seconds, preferably 30–60 seconds. The EFOS light guide 96 is positioned within the staging apparatus 12 at a distance of 0.25–3.0 inches from the cornea, optimally 0.25–1.0 inches. Exposures may range from 2500 mW×120 seconds to 4500 mW×45 seconds, preferably 2500 mW×75 seconds to 4500 mW×30 seconds (FIG. 13);

(9) Following the UV exposure, the cornea is thoroughly washed with 0.02M phosphate buffer at pH 7.2; and

Figure 14:
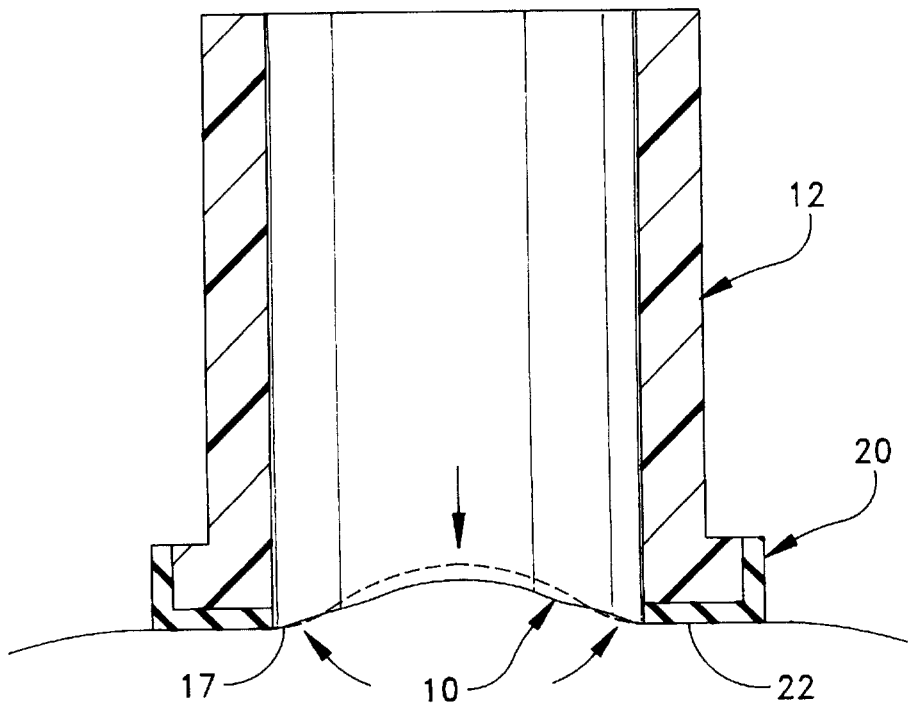

(10) The mold 36 and staging apparatus 12 are then removed from the eye and the eye is examined using slit lamp and corneal topography methods to determine the degree of change of curvature and to determine if additional shaping may be required (FIG. 14). The original curvature of the cornea is shown in FIG. 14 in broken line, while the new "emmetropic" curvature is shown in solid line.

Stabilization of Long Term Orthokeratology Patients

One of the anticipated benefits of the stabilization process is that it can be used to stabilize the corneas of patients having already undergone long term orthokeratology. The stabilization procedures will eliminate the need to continue wearing retainer lenses to maintain the shape of the cornea. While it may be possible to simply utilize the stabilization step for these patients, it is anticipated that the cornea will have to be destabilized before it can be restabilized to take on the new configuration. In such a method, the eye would be destabilized using the methodology as described above. Because the eye was already preshaped, very little shaping will be necessary to reshape the eye to the proper configuration. A mold would however be used to maintain the proper shape during the restabilization process. With the mold in place, the eye would then be exposed to a photoinitiator and exposed to UV light to restabilize the cornea in the new configuration.

Experiment 1

Experiments conducted using enucleated pig eyes. Pretreatment and post-treatment evaluations of eyes were made by slit-lamp examination and by taking K-readings. In a control portion of the experiment, several pig eyes were treated with contact lenses only. Neither destabilization nor stabilization were performed on the control eyes. As expected, there was no change in the corneal curvature as determined by slit-lamp examination and measurement of K-readings. In a second part of the experiment, contact lenses were applied to two eyes without destablization, followed by treatment with sodium persulfate solution (photochemical initiator) and exposure to UV light using an Ultracure 100SS Plus UV light source manufactured by EFOS of Williamsville, N.Y. The dosage of light was approximately 1500 mWatts for about 30 seconds (broad wavelength of 25–390 nm). Pretreatment measurements of the two eyes were 36.75/37.5. After treatment measurements were 43/41.5 and 40.5/44. The eyes were clear and the ridge created by the contact lens was visible after 1 hour. In a third part of the experiment, an eye was treated with a pH 8.76 phosphate buffer for 1 minute followed by exposure to 10 mg/ml glutaric anhydride in phosphate buffer for 1 minute to destabilize the cornea. A contact lens was applied. The eye was then flushed with phosphate buffer, pH 7.2 to remove residual glutaric acid and then soaked with phosphate buffer (0.02M), pH 8.0 containing 0.3M sodium persulfate. UV light was applied for 20 seconds, the lens removed and the eye again flushed with phosphate buffer, pH 7.2. The pretreatment measurements of the eye were 36.75/37.5. The pig eye was examined after the glutaric anhydride treatment and measurements were 40.5/39.0. After UV treatment, measurements were too steep to read and rather distorted. Indentations and ridges created by the lens were observed immediately post-treatment and 1 hour after treatment. Results showed definite curvature changes and very obvious ridges created by the lens.

Experiment 2

Second set of experiments also using enucleated pig eyes. an EYESYS topographical system was available to perform topographical mapping of the eyes before and after treatment. In addition, the EFOS Ultracure 100SS was available for UV light treatment. In a control part of the experiment, an eye was examined using a slit lamp and using the EYESYS system. Neither glutaric anhydride nor sodium persulfate were administered prior to application of UV light exposure. However, buffers were administered to simulate full treatment. EYESYS evaluation demonstrated that the surface characteristics following treatment remained the same as before treatment. In a second part of the experiment, a second pig eye was examined by slit lamp, and EYESYS. Topographical profiles were printed. The eye was them soaked in phosphate buffer at pH 8.5 for 2 minutes. Glutaric anhydride at 10 mg/ml was prepared in an alcohol solution and immediately administered to the eye. A contact lens was applied to the eye and held in place for 1 minute. The eye was then soaked in a sodium persulfate solution (0.3M sodium persulfate in pH 8.5 buffer) with the lens still in place. After several one (1) minute soaks in the sodium persulfate solution, the eye was exposed to UV light for about 30 seconds. The lens was removed and the eye washed with phosphate buffer, pH 7.2. The eye was then examined by slit lamp and EYESYS. Slit lamp examination showed that the eye had developed some cloudiness (probably due to the alcohol solution containing the glutaric anhydride). EYESYS examination demonstrated that the eye topography had been changed. In a third part of the experiment, a third eye was treated the same as above, expect that the glutaric anhydride was delivered in a phosphate buffer, pH 8.5, in an attempt to prevent the clouding observed using alcohol. Slit lamp examinations showed much less corneal clouding. EYESYS examinations demonstrated topographical changes appearing to match the curvature of the applied contact lens. The experiments show that the described techniques could alter the shape of the anterior curvature of the cornea.

Experiment 3

Third set of experiments using a live rabbit. Both the EYESYS topographical system and EFOS Ultracure 100SS were available. The rabbit's eyes were examined by slit-lamp and EYESYS. Topographical profiles were printed. The control eye was left untreated. The experimental eye was exposed to 0.02M phosphate buffer, pH 8.5, and treated with glutaric anhydride at 20 mg/ml in pH 8.5 phosphate buffer followed by application of a contact lens. The eye was then washed with 0.02M phosphate buffer, pH 8.5 to remove residual glutaric acid, soaked with buffer containing 0.3M sodium persulfate and exposed to UV light for two 30 second bursts with the contact lens in place. Both the control and treated eyes were examined by slit-lamp and EYESYS. Topographical profiles were printed. The treated eye showed and obvious change in surface topography. Slit-lamp examination indicated some corneal haze, which cleared in about 1 hour. The experiment, in a live animal, demonstrated that the anterior corneal curvature could be altered in a live subject using the described techniques.

It can therefore be seen that the instant invention provides a unique and effective method for quickly modifying the anterior curvature of the cornea with non-invasive surgical techniques. The three step process of destabilizing, shaping and restabilizing will allow potential patients to have the refractive vision errors corrected in a matter of hours, without a recovery period, rather than endure the lengthy and oftentimes painful procedures which currently exist. The unique method of restabilizing the cornea significantly decreases treatment time, and stabilizes the cornea in a corrected emmetropic configuration that will eliminate the need for retainer lenses or any other corrective lenses for that matter. As stated above, the unique aspects of the method are believed to reside in the unique three steps, destabilization, reshaping and stabilization and in the apparatus used to achieve the method. There has not been provided in the art a simple, non-surgical, non-invasive, and rapid treatment for refractive errors of the eyes, and the present invention is believed to have solved the problems of the prior art. For these reasons, the instant invention is believed to represent a significant advancement in the art which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A method of correcting refractive errors of the eye comprising the steps of:
    destabilizing the corneal tissue of the eye so that the anterior curvature of the cornea can be reshaped from a first configuration to a second desired configuration;
    shaping the softened cornea from the first configuration to the second desired configuration
    by applying a mold to the cornea and applying pressure thereto, said mold having a predetermined posterior curvature and configuration which engages with the anterior curvature of the cornea; and
    restabilizing the corneal tissues while the anterior curvature of the cornea is positioned in said second desired configuration.

2. The method of claim 1 wherein said step of destabilizing the corneal tissues comprises administering to the cornea a softening agent which is effective for destabilizing cross-linking between the collagen fibrils of the stroma of the cornea.

3. The method of claim 2 wherein said softening agent is selected from the group consisting of: anhydrides, acid chlorides, sulfonyl chlorides, sulfonic acids, and combinations thereof.

4. The method of claim 2 wherein said step of restabilizing the corneal tissues comprises exposing the corneal tissues to UV light energy.

5. The method of claim 4 further comprising the step of administering a photochemical initiator to the eye to rapidly initiate cross linking of the collagen matrix.

6. The method of claim 2 wherein said step of administering said chemical softening agent comprises the steps of positioning the lower rim of an annular staging device to the surface of the cornea so that the staging device encircles the area of the cornea to be treated, and administering the chemical softening agent into the interior of the staging device.

7. The method of claim 6 wherein the step of reshaping the cornea comprises positioning the mold within the staging device and applying downward pressure for a predetermined period of time.

8. The method of claim 7 wherein said mold is fabricated from a transparent and ultraviolet light transmittable material, and said step of restabilizing the corneal tissues comprises positioning an ultraviolet light source within the staging device on top of the mold and energizing the light source for a predetermined period of time whereby UV light passes through the mold to the corneal tissues.

9. The method of claim 8 further comprising the step of administering a photochemical activating agent to the cornea prior to exposing the cornea to said dosage of ultraviolet light.

10. The method of claim 6 wherein said step of restabilizing the corneal tissues comprises positioning an ultraviolet light source within the staging device and energizing the light source for a predetermined period of time whereby light is directed onto the corneal tissues.

11. The method of claim 10 further comprising the step of administering a photochemical activating agent to the cornea prior to exposing the cornea to said dosage of ultraviolet light.

12. A method of correcting refractive errors of the eye comprising the steps of:
    positioning the lower rim of an annular staging device to the surface of the cornea so that the staging device encircles the area of the cornea to be treated;
    administering a chemical softening agent into the interior of the staging device wherein said chemical softening agent is effective for destabilizing cross-linking between the collagen fibrils of the stroma of the cornea so that the anterior curvature of the cornea can be reshaped from a first configuration to a second desired configuration;
    reshaping the softened cornea from the first configuration to the second desired configuration by applying a mold to the cornea, said mold having a predetermined posterior curvature and configuration which engages with the anterior curvature of the cornea, said mold being positioned within the staging device and thereafter having downward pressure applied for a predetermined period of time to achieve said reshaping; and
    restabilizing the corneal tissues while the anterior curvature of the cornea is positioned in said second desired configuration by exposing the corneal tissues to a predetermined dosage of ultraviolet light.

13. The method of claim 12 wherein said mold is fabricated from a transparent and ultraviolet light transmittable material, and said step of restabilizing the corneal tissues comprises positioning an ultraviolet light source within the staging device on top of the mold and energizing the light source for a predetermined period of time whereby light passes through the mold to the corneal tissues.

* * * * *